(12) United States Patent
Ding et al.

(10) Patent No.: US 11,524,987 B2
(45) Date of Patent: Dec. 13, 2022

(54) HIGHLY PURIFIED RECOMBINANT HUMAN INSULIN (RHI) API AND METHODS OF PRODUCING THE SAME

(71) Applicant: Amphastar Pharmaceuticals, Inc., Rancho Cucamonga, CA (US)

(72) Inventors: Jie Fei Ding, Riverside, CA (US); Aili Bo, La Verne, CA (US); Jack Yongfeng Zhang, Diamond Bar, CA (US); Mary Zi-ping Luo, Diamond Bar, CA (US); Zhongli Bao, Chino Hills, CA (US)

(73) Assignee: AMPHASTAR PHARMACEUTICALS, INC., Rancho Cucamonga, CA (US)

( * ) Notice: Subject to any disclaimer, the term of this patent is extended or adjusted under 35 U.S.C. 154(b) by 188 days.

(21) Appl. No.: 16/583,125

(22) Filed: Sep. 25, 2019

(65) Prior Publication Data

US 2020/0216511 A1    Jul. 9, 2020

Related U.S. Application Data

(60) Provisional application No. 62/736,415, filed on Sep. 25, 2018.

(51) Int. Cl.

| | | |
|---|---|---|
| C07K 14/62 | (2006.01) | |
| B01D 9/00 | (2006.01) | |
| B01D 15/18 | (2006.01) | |
| B01D 15/32 | (2006.01) | |
| B01D 15/36 | (2006.01) | |
| C07K 1/06 | (2006.01) | |
| C07K 1/16 | (2006.01) | |
| C07K 1/18 | (2006.01) | |
| C07K 1/30 | (2006.01) | |
| C07K 1/36 | (2006.01) | |

(52) U.S. Cl.
CPC ............ C07K 14/62 (2013.01); B01D 9/0059 (2013.01); B01D 15/1871 (2013.01); B01D 15/325 (2013.01); B01D 15/363 (2013.01); C07K 1/063 (2013.01); C07K 1/16 (2013.01); C07K 1/18 (2013.01); C07K 1/306 (2013.01); C07K 1/36 (2013.01); C07B 2200/13 (2013.01)

(58) Field of Classification Search
CPC . C07K 14/62; C07K 1/18; C07K 1/16; C07K 1/36; B01D 9/0059; B01D 15/363
See application file for complete search history.

(56) References Cited

U.S. PATENT DOCUMENTS

| | | |
|---|---|---|
| 2008/0146492 A1 | 6/2008 | Zimmerman et al. |
| 2014/0213756 A1 | 7/2014 | Zimmerman et al. |

FOREIGN PATENT DOCUMENTS

| | | | |
|---|---|---|---|
| DE | 60018785 T2 | 2/2006 | |
| WO | 2001031336 A2 | 5/2001 | |
| WO | WO-2006125765 A2 * | 11/2006 | ............ A61K 38/28 |
| WO | 2014122651 A1 | 8/2014 | |
| WO | 2016144658 A1 | 9/2016 | |

OTHER PUBLICATIONS

The International Bureau of WIPO, International Preliminary Report on Patentability issued in International Application No. PCT/US2019/053029, dated Apr. 8, 2021, 13 pages.
European Patent Office, International Search Report issued in PCT/US2019/053029, dated Feb. 28, 2020, 5 pages.
European Patent Office, Written Opinion issued in PCT/US2019/053029, dated Feb. 28, 2020, 11 pages.

* cited by examiner

*Primary Examiner* — Jeanette M Lieb
(74) *Attorney, Agent, or Firm* — Lewis Roca Rothgerber Christie LLP

(57) ABSTRACT

Methods are disclosed for producing highly purified recombinant human insulin (RHI) having a purity of 99.0% (w/w) or greater, a Total Impurity (not including the related substance desamido Asn$^{A21}$-RHI, as specified by USP) of 0.8% (w/w) or less, and an impurity C of 0.1% (w/w) or less. Also disclosed are API compositions of highly purified RHI having a purity of 99.0% (w/w) or greater, a Total Impurity of 0.8% (w/w) or less, and an impurity C of 0.1% (w/w) or less.

35 Claims, 12 Drawing Sheets

Specification includes a Sequence Listing.

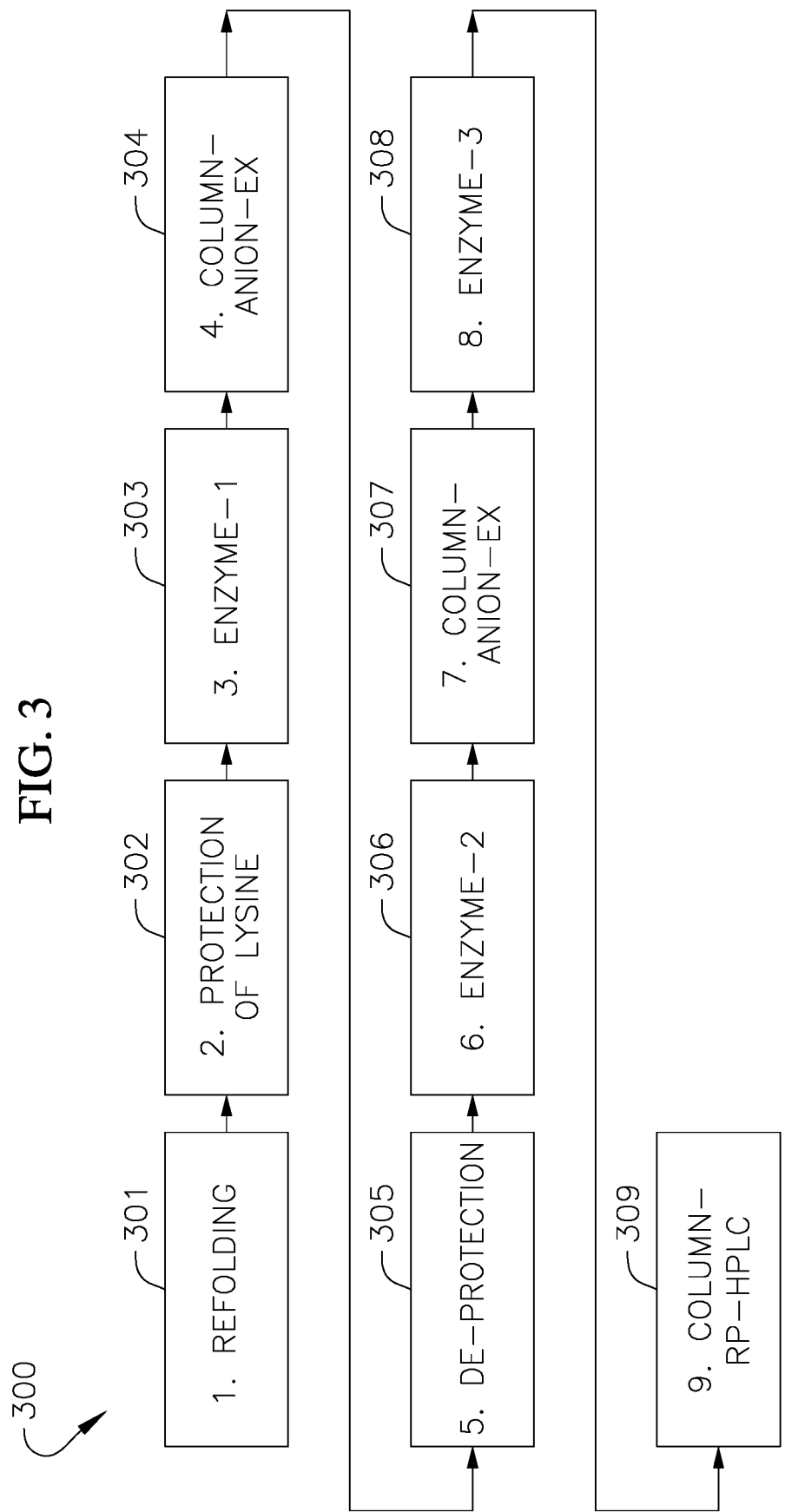

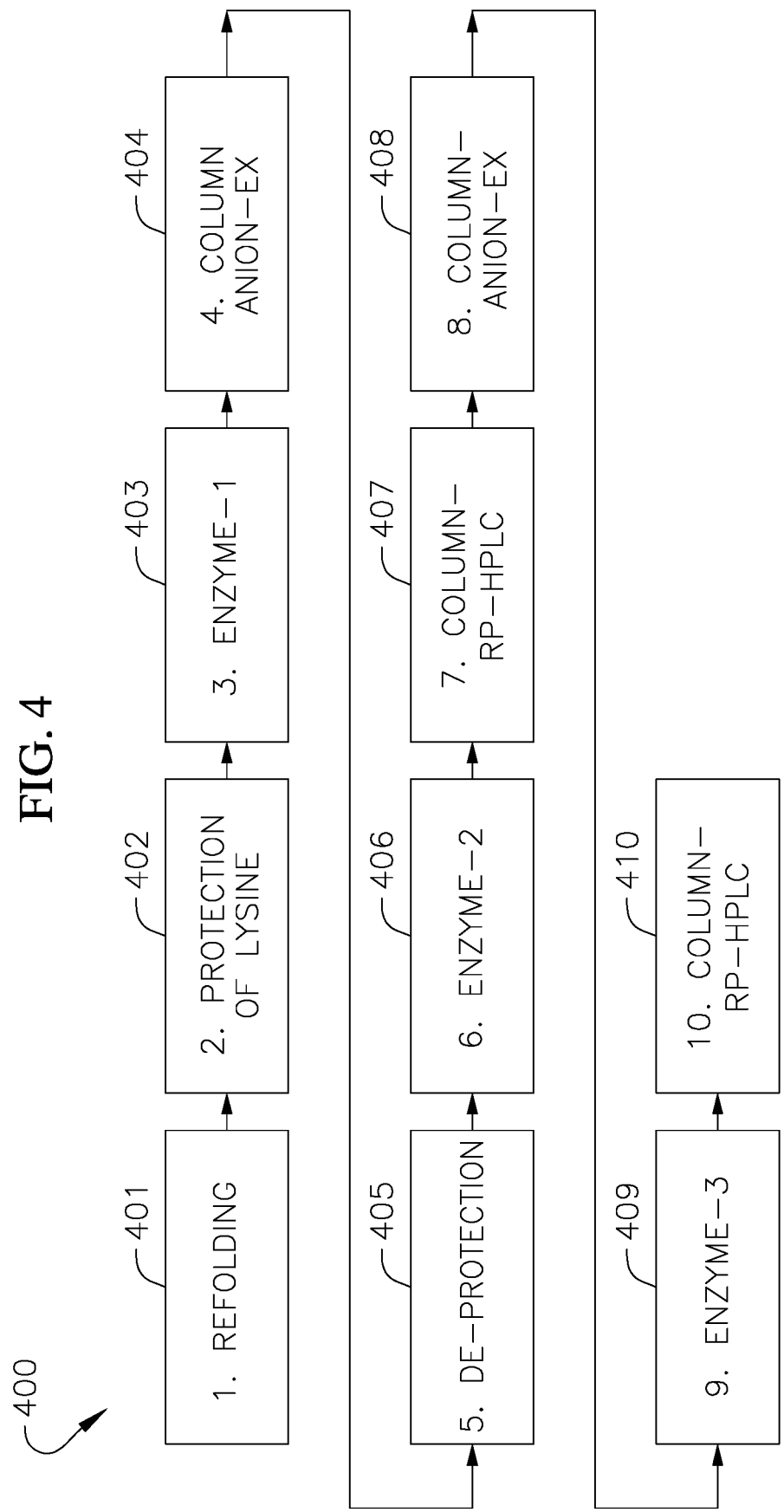

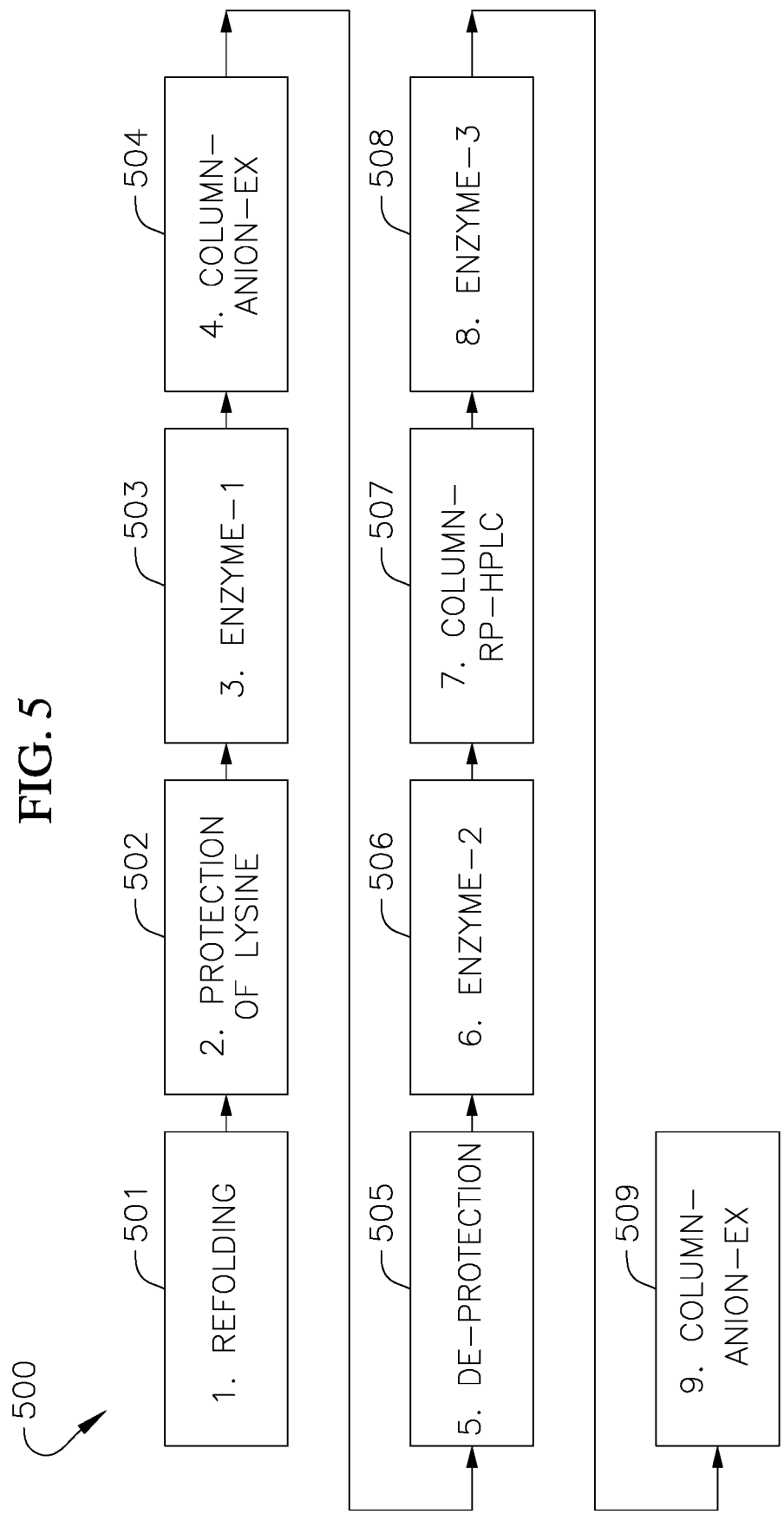

HIGHLY PURIFIED RECOMBINANT HUMAN INSULIN (RHI) API AND METHODS OF PRODUCING THE SAME

CROSS-REFERENCE TO RELATED APPLICATION

The present application claims priority to and the benefit of U.S. Provisional Application No. 62/736,415, filed on Sep. 25, 2018, the entire contents of which is incorporated herein by reference.

INCORPORATION BY REFERENCE

The instant application contains a Sequence Listing which has been submitted in ASCII format via EFS-Web and is hereby incorporated by reference in its entirety. Said ASCII copy, was created on Dec. 2, 2021, is named 180244SEQ-LISTING-4.txt, and is 7,268 bytes in size.

TECHNICAL FIELD

The present disclosure introduces methods for producing highly purified recombinant human insulin (RHI) and compositions thereof. The highly purified RHI is suitable for use as an active pharmaceutical ingredient (API) for RHI drug products.

BACKGROUND

Human insulin is a hormone that regulates glucose metabolism. The human insulin protein consists of two polypeptide chains—an A-chain of 21 amino acids (SEQ ID NO: 1) and a B-chain of 30 amino acids (SEQ ID NO: 2) for a total of 51 amino acids. The A and B polypeptide chains are linked by disulfide bonds between A-chain cysteines paired with a respective B-chain cysteine. The disulfide bonds and corresponding cysteines (Cys) are $Cys^{A7}$-$Cys^{B7}$, $Cys^{A20}$-$Cys^{B19}$, and $Cys^{A6}$-$Cys^{A11}$. Recombinant human insulin is indicated as a therapeutic composition for patients with diabetes. Diabetes mellitus is characterized by elevated blood glucose levels as a result of insulin deficiency and/or increased hepatic glucose production. Recombinant human insulin may be administered to a patient by subcutaneous or intravenous injection.

The basic techniques of synthesizing recombinant human insulin API using recombinant DNA technology are generally known in the art. But the technical challenge of implementing these basic techniques into a robust production/synthesis process remains a difficult technical challenge because of the different types and amounts of impurities that are produced during the production process of recombinant human insulin API. Also, different pharmaceutical companies may produce different impurities during the recombinant human insulin production/synthesis because different companies may use different production process strategies, different starting materials such as different sequences of the single-chain precursor (SCP), different expression host cells for gene expression, among other factors. Throughout this disclosure, "human insulin" or "insulin" may be used interchangeably and synonymously with "recombinant human insulin" or "RHI."

The RHI drug products currently on the market contain certain level of impurities. The typical level of total impurities (not including the related substance desamido $Asn^{A21}$-human insulin ("desamido $Asn^{A21}$-RHI"), as specified by the United States Pharmacopeia (USP) for RHI) is in the range of about 1-2% (w/w). Some of these total impurities are generated in the finished RHI drug product (e.g. solution), which may increase as a function of time, and some of these total impurities exist in the API. Therefore, an RHI API with less impurity will provide a basis for RHI drug products with less impurity. Accordingly, an RHI API with high purity is needed in the art. This disclosure is directed at a process to generate RHI API with a Total Impurity (not including the related substance desamido $Asn^{A21}$-RHI, as specified by USP) of not more than 0.8% (w/w) based on the total weight of the RHI API, hereinafter referred to as "highly purified recombinant human insulin API," or "highly purified RHI API."

In addition, certain impurities may be difficult to remove, such as acetylated lysine at position 31 of the B-chain ($Lysine^{B31}$, $Lys^{B31}$, or $K^{B31}$) of the RHI, denoted as "Impurity C" or "impurity C" herein. In particular, prior to the processing of SCP to RHI, the impurity C precursor can be as high as about 2-3% (w/w) in the SCP batch. An example of an impurity C precursor is acetylated $Lys^{C1}$ in the SCP, which may have been developed during the synthesis of SCP. The synthesis of the SCP, consisting of A-Chain, B-Chain, C-peptide, and leading sequence, could be performed using the master host cell (i.e. E. coli) through the fermentation process developed by Ferring International Center S. A. (Ferring). See, e.g., Ferring's European Patent No. EP0871474B1, entitled "Generation of Human Insulin," filed Dec. 29, 1994, and granted Mar. 1, 2007. The present disclosure seeks to continue and significantly improve upon such work by Ferring, such as significantly reducing total impurities (not including the related substance desamido $Asn^{A21}$-RHI, as specified by USP) and impurity C in order to produce highly purified RHI for use as an API.

Even after the application of several purification actions during the processing of the SCP to RHI, impurity C can still be as high as 0.7% (w/w) as an impurity in the final purified RHI API composition. Therefore, a technical solution to reducing the amount of impurity C during the production/synthesis of RHI is needed in order to produce highly purified RHI API. Accordingly, the present disclosure solves this technical problem by presenting methods for producing RHI API having a purity of 99.0% (w/w) or greater, a total impurity (not including the related substance desamido $Asn^{A21}$-RHI) of 0.8% or less, and impurity C of 0.1% (w/w) or less, based on the total weight of the RHI API. The present disclosure also presents compositions of RHI API having a purity of 99.0% (w/w) or greater, a total impurity (not including the related substance desamido $Asn^{A21}$-RHI) of 0.8% or less, and impurity C of 0.1% (w/w) or less, based on the total weight of the RHI API. Additionally, the present disclosure introduces compositions of, and methods for producing RHI API having a purity of 99.0% (w/w) or greater, a total impurity (not including the related substance desamido $Asn^{A21}$-RHI) of 0.8% or less, impurity C of 0.1% (w/w) or less, and impurity E of 0.2% (w/w) or less, based on the total weight of the RHI API.

SUMMARY

Exemplary embodiments of the present disclosure address at least the above problems and/or disadvantages and advance the art by providing at least the advantages described below. Additional objects, advantages, and salient features of exemplary embodiments of the present disclosure will become apparent to those skilled in the art from the following detailed description, which, taken in conjunction with the annexed drawings, discloses exemplary embodiments of the present disclosure.

Methods for Producing Highly Purified RHI API

First, the present disclosure provides methods for producing highly purified recombinant human insulin (RHI) active pharmaceutical ingredient (API) having a purity of 99.0% (w/w) or more, a Total Impurity of 0.8% (w/w) or less, and an impurity C of 0.1% (w/w) or less, based on the total weight of the RHI API. The Total Impurity does not include desamido $Asn^{A21}$-RHI, and impurity C is an acetylated $Lys^{B31}$-RHI.

In a preferred embodiment, the methods introduced in this present disclosure produce highly purified RHI API, in solid form, having a purity of 99.0% (w/w) or more, a Total Impurity of 0.8% (w/w) or less, and an impurity C of 0.1% (w/w) or less, based on the total weight of the highly purified RHI API in a solid form. In other embodiments, the disclosed methods produce RHI API, in a liquid form, having a purity of 99.0% (w/w) or more, a Total Impurity of 0.8% (w/w) or less, and an impurity C of 0.1% (w/w) or less, based on the total weight of the RHI API in the liquid form. Additionally, the disclosed methods produce RHI API having a purity of 99.0% (w/w) or greater, a total impurity (not including the related substance desamido $Asn^{A21}$-RHI) of 0.8% or less, impurity C of 0.1% (w/w) or less, and impurity E of 0.2% (w/w) or less, based on the total weight of the RHI API, in a solid form or a liquid form.

As defined herein, "highly purified recombinant human insulin API" or "highly purified RHI API" means recombinant human insulin API (solid form or liquid form) with a Total Impurity of 0.8% (w/w) or less based on the total weight of the RHI API. "Total Impurity" or "Total Impurities" means all impurities in the RHI API except for the related substance desamido $Asn^{A21}$-RHI. For brevity herein, RHI API having a Total Impurity of 0.8% (w/w) or less based on the total weight of the RHI API, is deemed "highly purified RHI API." For example, RHI API having a purity of 99.0% (w/w) or more, a Total Impurity of 0.8% (w/w) or less, and an impurity C of 0.1% (w/w) or less, based on the total weight of the RHI API, is deemed "highly purified RHI API." As will be described herein, the highly purified RHI API is the highly purified RHI API produced using the methods introduced in this present disclosure. The USP guidance on RHI specifies that the total impurities of RHI do not include the related substance desamido $Asn^{A21}$-RHI.

In some embodiments, the methods for producing highly purified RHI API comprise:

protecting two Lysine residues on a single-chain precursor (SCP) using a Lysine protecting group, wherein the SCP has a formula of [(Leader Peptide)-(B-Chain)-(C-peptide)-(A-Chain)], wherein the C-peptide is a short peptide consisting of $Arg^{C2}$-$Lys^{C1}$ (SEQ ID NO: 3), wherein the two Lysine residues is a first Lysine residue at a first residue of the C-peptide (C1) of the SCP ($Lys^{C1}$), and a second Lysine residue at residue 28 of the B-chain (B28) of the SCP ($Lys^{B28}$);

enzyme-cleaving the SCP to produce an $Arg^{C2}$-$Lys^{C1}$-RHI;

applying a first column purification action to separate the Leader Peptide from the $Arg^{C2}$-$Lys^{C1}$-RHI to generate $Arg^{C2}$-$Lys^{C1}$-RHI;

enzyme-cleaving a half of the C-peptide in the $Arg^{C2}$-$Lys^{C1}$-RHI to produce $Lys^{C1}$-RHI and an Impurity C, wherein the Impurity C is acetylated $Lys^{B31}$-RHI;

de-protecting the two Lysine residues in the $Lys^{C1}$-RHI;

applying a second column purification action to separate one or more impurities from the $Lys^{C1}$-RHI;

applying a third column purification action to the $Lys^{C1}$-RHI to reduce an amount of the Impurity C in the $Lys^{C1}$-RHI to 0.1% (w/w) or less based on the total weight of the $Lys^{C1}$-RHI;

enzyme-cleaving the $Lys^{C1}$-RHI to produce $Lys^{C1}$ and the RHI; applying a fourth column purification action to separate one or more impurities from the RHI to produce highly purified RHI for use as an API; and crystallizing the highly purified RHI API to produce highly purified RHI API in a solid form;

wherein the method produces highly purified RHI API, in a solid form, having a purity of 99.0% (w/w) or more, a total impurity of 0.8% (w/w) or less, wherein the total impurity does not include desamido $Asn^{A21}$-RHI, and the Impurity C of 0.1% (w/w) or less, and wherein w/w denotes weight by weight and is based on the total weight of the highly purified RHI API in the solid form.

In other embodiments, the methods produce highly purified RHI API, in a solid form, having a purity of 99.3% (w/w) or more, a Total Impurity of 0.5% (w/w) or less, and impurity C of 0.1% (w/w) or less, all based on the total weight of the highly purified RHI API in the solid form. The purity and impurity percentages (w/w) of the highly purified RHI API in the solid form can be assessed shortly after the highly purified RHI API is crystallized into the solid form, such as within 6, 12, 24, 48, or 72 hours after the highly purified RHI API is crystallized into the solid form.

In still other embodiments, the methods can produce highly purified RHI API in a liquid form, having a purity of 99.3% (w/w) or more, a Total Impurity of 0.5% (w/w) or less, and impurity C of 0.1% (w/w) or less, all based on the total weight of the highly purified RHI API in the liquid form. The purity and impurity percentages (w/w) of the highly purified RHI API in the liquid form can be assessed shortly after the final purification action, such as within 6, 12, 24, 48, or 72 hours after the final purification action. Action 111 in method 100 is an exemplary embodiment of such final purification action. In some embodiments of the methods of the present disclosure, the enzyme-cleaving of the SCP to produce the $Arg^{C2}$-$Lys^{C1}$-RHI comprises applying trypsin to the $Arg^{C2}$-$Lys^{C1}$-RHI. In some embodiments of the methods, the step of enzyme-cleaving the $Arg^{C2}$-$Lys^{C1}$-RHI to produce $Lys^{C1}$-RHI and an impurity C comprises applying carboxypeptidase B (CPB) to the $Arg^{C2}$-$Lys^{C1}$-RHI. In some embodiments of the methods, the step of enzyme-cleaving the $Lys^{C1}$-RHI to produce RHI also comprises applying CPB to the $Lys^{C1}$-RHI.

In some embodiments of the methods, the first column purification action utilizes anion-exchange column chromatography. In some embodiments of the methods, the second column purification action utilizes anion-exchange column chromatography. In other embodiments of the methods, the third column purification action utilizes RP-HPLC for reducing the amount of the impurity C in the $Lys^{C1}$-RHI to 0.1% (w/w) or less on the total weight of the $Lys^{C1}$-RHI, which in turn, enables the production of highly purified RHI API having impurity C of 0.1% (w/w) or less based on the total weight of the highly purified RHI API, as described herein. In other embodiments of the methods, the fourth column purification action utilizes RP-HPLC.

In some embodiments, the third column purification action and the fourth column purification action each utilizes RP-HPLC. In some embodiments, the third column purification action and the fourth column purification action each utilizes RP-HPLC having a C18 column. In other embodiments, the third column purification action and the fourth column purification action each utilizes RP-HPLC having a C8 column.

In some embodiments of the methods, the third column purification action that reduces the amount of the impurity C in the $Lys^{C1}$-RHI to 0.1% (w/w) or less, comprises applying reverse-phase high performance liquid chromatography (RP-HPLC) utilizing a C18 column to separate the impurity C from the $Lys^{C1}$-RHI. In other embodiments of the methods, this third column purification action further includes utilizing an aqueous solution comprising $(NH_4)_2SO_4$, isopropyl alcohol (IPA), or a combination thereof in the RP-HPLC. In still other embodiments of the methods, this third column purification action further includes applying a pH of about 2.5 to about 3.0 in the RP-HPLC. In some embodiments of the methods, this third column purification action utilizes RP-HPLC having a preparation column, such as a preparation column having a length of about 250 mm and an internal diameter of about 10.0 mm. In other embodiments of the methods, this third column purification action further utilizes RP-HPLC having a semi-preparation column, such as a preparation column having a length of about 250 mm and an internal diameter of about 21.2 mm.

In some embodiments, the methods further comprise refolding the SCP using a refolding buffer. In other embodiments, the methods further comprise, optionally, removing the trypsin using aprotinin.

In some embodiments, the one or more impurities separated by the second column purification action include at least $Arg^{C2}$. In some embodiments, the one or more impurities separated by the fourth column purification action include at least $Lys^{C1}$. At each column purification action, the one or more impurities separated may include those commonly known in the art as well as the impurities identified herein, including the impurities identified in the Tables 1-6. Note that the separation of impurities may include the type of impurities, the amount of the impurities, or the combination thereof.

In other embodiments, the method for producing highly purified RHI API comprises:

protecting at least two Lysine residues on a single-chain precursor (SCP) using a Lysine protecting group, wherein the SCP has a formula of [(Leader Peptide)-(B-Chain)-(C-peptide)-(A-Chain)], wherein the C-peptide comprises at least $Arg^{C2}$-$Lys^{C1}$ wherein the Lysine residues comprise a first Lysine residue at a first residue of the C-peptide (C1) of the SCP ($Lys^{C1}$), and a second Lysine residue at residue 28 of the B-chain (B28) of the SCP ($Lys^{B28}$);

enzyme-cleaving the $Arg^{C2}$-$Lys^{C1}$-RHI to produce $Lys^{C1}$-RHI and an Impurity C, wherein the Impurity C is acetylated $Lys^{B31}$-RHI;

de-protecting the Lysine residues in $Lys^{C1}$-RHI;

applying a plurality of column purification actions to produce highly purified RHI for use as an API, wherein at least one of the column purification actions reduces an amount of the Impurity C in the $Lys^{C1}$-RHI to 0.1% (w/w) or less based on the total weight of the $Lys^{C1}$-RHI;

enzyme-cleaving the $Lys^{C1}$-RHI to produce RHI; and crystallizing the highly purified RHI API to produce highly purified RHI API in a solid form;

wherein the method produces highly purified RHI API, in a solid form, having a purity of 99.0% (w/w) or more, a total impurity of 0.8% (w/w) or less, wherein the total impurity does not include desamido $Asn^{A21}$-RHI, and the impurity C of 0.1% (w/w) or less, and wherein w/w denotes weight by weight and is based on the total weight of the highly purified RHI API in the solid form.

In still other embodiments, the method for producing highly purified recombinant human insulin (RHI) comprises:

protecting at least two Lysine residues on a single-chain precursor (SCP) using a Lysine protecting group, wherein the SCP has a formula of [(Leader Peptide)-(B-Chain)-(C-peptide)-(A-Chain)], wherein the C-peptide comprises at least $Arg^{C2}$-$Lys^{C1}$, wherein the Lysine residues comprise a first Lysine residue at a first residue of the C-peptide (C1) of the SCP ($Lys^{C1}$), and a second Lysine residue at residue 28 of the B-chain (B28) of the SCP ($Lys^{B28}$);

enzyme-cleaving the $Arg^{C2}$-$Lys^{C1}$-RHI to produce $Lys^{C1}$-RHI and an Impurity C, wherein the Impurity C is acetylated $Lys^{B31}$-RHI;

de-protecting the Lysine residues in $Lys^{C1}$-RHI;

applying a plurality of column purification actions to produce highly purified RHI for use as an API, wherein at least one of the column purification actions reduces an amount of the Impurity C in the $Lys^{C1}$-RHI to 0.1% (w/w) or less based on the total weight of the $Lys^{C1}$-RHI; and enzyme-cleaving the $Lys^{C1}$-RHI to produce RHI;

wherein the method produces highly purified RHI API, in a liquid form, having a purity of 99.0% (w/w) or more, a total impurity of 0.8% (w/w) or less, wherein the total impurity does not include desamido $Asn^{A21}$-RHI, and the impurity C of 0.1% (w/w) or less, and wherein w/w denotes weight by weight and is based on the total weight of the highly purified RHI API in the liquid form.

In some embodiments, the plurality of column purification actions include:

a first column purification action to separate at least the Leader Peptide Sequence from the $Arg^{C2}$-$Lys^{C1}$-RHI, wherein the first column purification action occurs after the step of enzyme-cleaving the SCP to produce the $Arg^{C2}$-$Lys^{C1}$-RHI but before the step of enzyme-cleaving the $Arg^{C2}$-$Lys^{C1}$-RHI to produce the $Lys^{C1}$-RHI and the Impurity C;

a second column purification action to separate at least an $Arg^{C2}$ from the $Lys^{C1}$-RHI, wherein the second purification action separates one or more impurities after the step of de-protecting the Lysine residues in the $Lys^{C1}$-RHI;

a third column purification action, which is the column purification action that reduces the amount of the Impurity C to 0.1% (w/w) or less in the $Lys^{C1}$-RHI, and this third column purification action occurs after the step of de-protecting the Lysine residues in the $Lys^{C1}$-RHI but before the step of enzyme-cleaving of the $Lys^{C1}$-RHI to produce the RHI; and a fourth column purification action to separate at least $Lys^{C1}$ from the RHI, wherein the fourth column purification action occurs after the step of cleaving the $Lys^{C1}$-RHI.

Additionally, the disclosed method further reduces an amount of impurity E to 0.2% (w/w) or less, the impurity E is $Thr^{B30}$ deletion-RHI, thereby producing highly purified RHI API, in a solid form or a liquid form, having a purity of 99.0% (w/w), Total Impurity of 0.8% (w/w) or less, impurity C of 0.1% (w/w) or less, and impurity E of 0.2% (w/w) or less, based on the total weight of the highly purified RHI API in the solid form or the liquid form, respectively. In still other embodiments, the method produces highly purified RHI API, in solid form or liquid form, having a purity of 99.3% (w/w) or more, a Total Impurity of 0.5% (w/w) or less, an impurity C of 0.1% (w/w) or less, and an impurity E of 0.2% (w/w) or less, and wherein w/w denotes weight by weight of the API and is based on the total weight of the highly purified RHI API, in solid form or liquid form, respectively.

In some embodiments, the disclosed method reduces the amount of impurity C to 0.1% (w/w) or less based on the total weight of the highly purified RHI API, including but not limited to, 0.09% (w/w) or less, 0.08% (w/w) or less, 0.07% (w/w) or less, 0.06% (w/w) or less, 0.05% (w/w) or less, 0.04% (w/w) or less, 0.03% (w/w) or less, 0.02% (w/w) or less, 0.01% (w/w) or less, or not detected. In other embodiments, the Impurity C is acetylated Lys$^{B31}$-RHI. In still other embodiments, the Impurity C comprises acetylated Lys$^{B31}$-RHI.

In other embodiments, the disclosed method reduces an amount of impurity E to 0.25% (w/w) or less based on the total weight of the highly purified RHI API, including but not limited to, 0.24% (w/w) or less, 0.23% (w/w) or less, 0.22% (w/w) or less, 0.21% (w/w) or less, 0.20% (w/w) or less, 0.19% (w/w) or less, 0.18% (w/w) or less, 0.17% (w/w) or less, 0.16% (w/w) or less, 0.15% (w/w) or less, 0.14% (w/w) or less, 0.13% (w/w) or less, 0.12% (w/w) or less, 0.11% (w/w) or less, 0.10% (w/w) or less, 0.09% (w/w) or less, 0.05% (w/w) or less, 0.04% (w/w) or less, 0.03% (w/w) or less, 0.02% (w/w) or less, 0.01% (w/w) or less, or not detected.

Compositions of Highly Purified RHI API

Second, the present disclosure also provides compositions for active pharmaceutical ingredient (API) comprising highly purified recombinant human insulin (RHI), in solid form or liquid form, having a purity of 99.0% (w/w) or more, a Total Impurity of 0.8% (w/w) or less, and an impurity C of 0.1% (w/w) or less, and wherein w/w denotes weight by weight of the API and is based on the total weight of the highly purified RHI API, in solid form or liquid form, respectively. As disclosed herein, the Total Impurity does not include the related substance desamido Asn$^{A21}$-RHI$^-$, and impurity C is acetylated Lys$^{B31}$-RHI.

In some embodiments of the compositions, the highly purified RHI API, in solid form or liquid form, has a purity of 99.3% (w/w) or more, a Total Impurity of 0.5% (w/w) or less, and an impurity C of 0.1% (w/w) or less, and wherein w/w denotes weight by weight of the API and is based on the total weight of the highly purified RHI API, in solid form or liquid form, respectively.

In still other embodiments of the compositions, the highly purified RHI API, in solid form or liquid form, has a purity of 99.0% (w/w) or more, a Total Impurity of 0.8% (w/w) or less, an impurity C of 0.1% (w/w) or less, and an impurity E of 0.2% (w/w) or less, and wherein w/w denotes weight by weight of the API and is based on the total weight of the highly purified RHI API, in solid form or liquid form, respectively. In other embodiments of the compositions, the highly purified RHI API, in solid form or liquid form, has a purity of 99.3% (w/w) or more, a Total Impurity of 0.5% (w/w) or less, an impurity C of 0.1% (w/w) or less, and an impurity E of 0.2% (w/w) or less, and wherein w/w denotes weight by weight of the API and is based on the total weight of the highly purified RHI API, in solid form or liquid form, respectively.

In some embodiments, the API composition is in a solid form. The purity and impurity percentages (w/w) of the highly purified solid RHI API can be assessed shortly after the highly purified liquid RHI API is crystallized into solid form, such as within 6, 12, 24, 48, or 72 hours after the highly purified liquid RHI API is crystallized into solid form. In other embodiments, the highly purified RHI API composition is in a liquid form, such as in an aqueous form. The purity and impurity percentages (w/w) of the highly purified liquid RHI API can be assessed shortly after the final purification action, such as within 6, 12, 24, 48, or 72 hours after the final purification action. An exemplary embodiment of a final purification action is action 111 in method 100. Exemplary embodiments of these highly purified RHI API compositions are provided in Examples 1-8 and these API compositions can be produced using method 100. Disclosed compositions of highly purified RHI API can be for RHI drug products, such as RHI aqueous solutions for subcutaneous or intravenous injection.

In still other embodiments of the compositions, the highly purified RHI API has an amount of impurity C of 0.1% (w/w) or less based on the total weight of the highly purified RHI API, including but not limited to, 0.09% (w/w) or less, 0.08% (w/w) or less, 0.07% (w/w) or less, 0.06% (w/w) or less, 0.05% (w/w) or less, 0.04% (w/w) or less, 0.03% (w/w) or less, 0.02% (w/w) or less, 0.01% (w/w) or less, or not detected.

In other embodiments of the compositions, the highly purified RHI API has an amount of impurity E of 0.25% (w/w) or less based on the total weight of the highly purified RHI API, including but not limited to, 0.24% (w/w) or less, 0.23% (w/w) or less, 0.22% (w/w) or less, 0.21% (w/w) or less, 0.20% (w/w) or less, 0.19% (w/w) or less, 0.18% (w/w) or less, 0.17% (w/w) or less, 0.16% (w/w) or less, 0.15% (w/w) or less, 0.14% (w/w) or less, 0.13% (w/w) or less, 0.12% (w/w) or less, 0.11% (w/w) or less, 0.10% (w/w) or less, 0.09% (w/w) or less, 0.05% (w/w) or less, 0.04% (w/w) or less, 0.03% (w/w) or less, 0.02% (w/w) or less, 0.01% (w/w) or less, or not detected.

BRIEF DESCRIPTION OF THE FIGURES

The above and other exemplary features and advantages of certain exemplary embodiments of the present disclosure will become more apparent from the following description of certain exemplary embodiments thereof when taken in conjunction with the accompanying drawings in which:

FIG. 3 is a process flow chart depicting Comparative Example 1 for a method of producing RHI API with less purity.

FIG. 4 is a process flow chart depicting Comparative Example 2 for a method of producing RHIAPI with less purity.

FIG. 5 is a process flow chart depicting Comparative Example 3 for a method of producing RHIAPI with less purity.

Throughout the drawings, like reference numerals will be understood to refer to like elements, features and structures.

DETAILED DESCRIPTION

Figure 1:
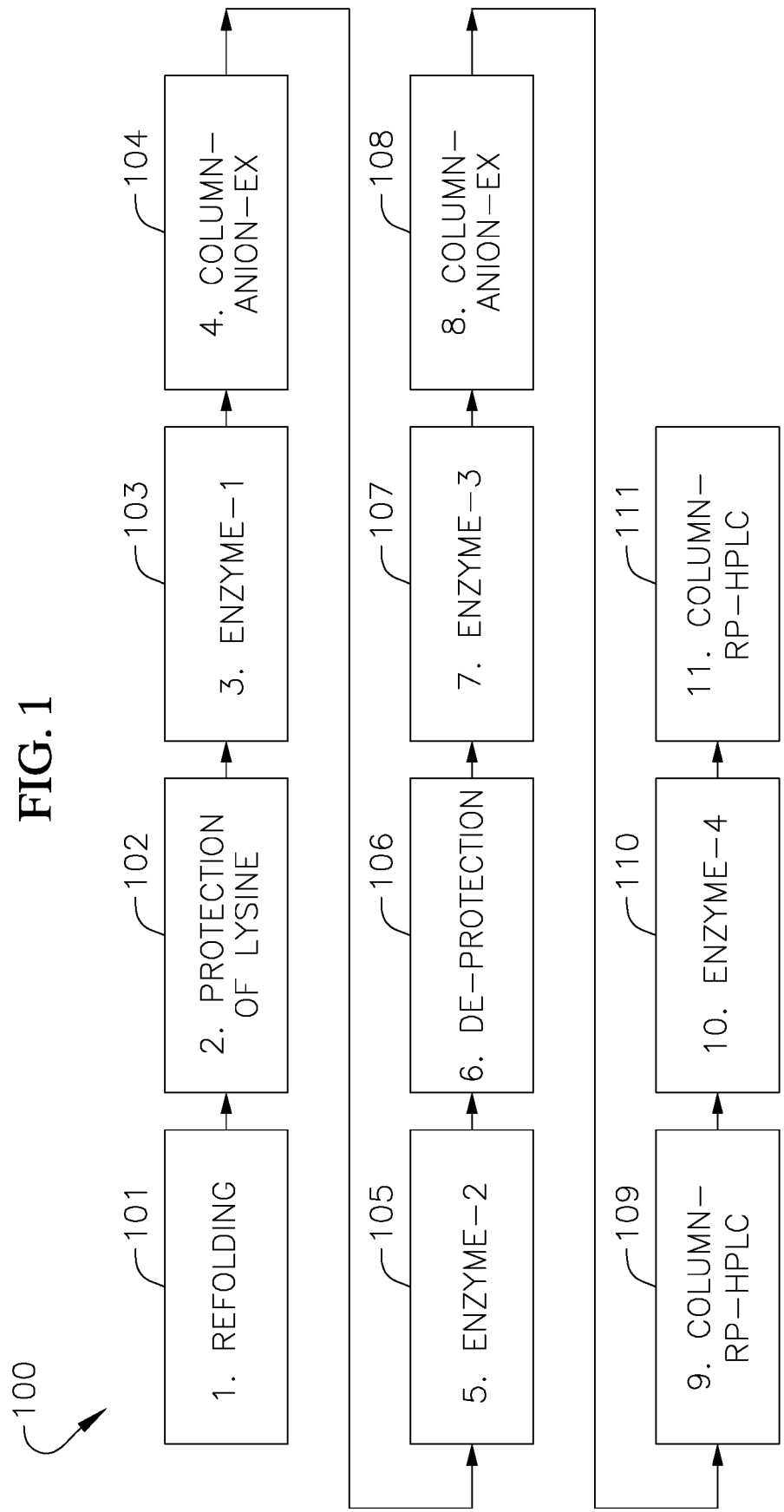
FIG. 1 is a process flow chart illustrating an exemplary embodiment of the disclosed methods, depicted as method 100, for producing highly purified RHI API.

The matters exemplified in the present disclosure are provided to assist in a comprehensive understanding of exemplary embodiments of the present disclosure with reference to the accompanying drawing figures. While the present disclosure has been described in connection with certain embodiments, it is to be understood that the disclosure is not limited to the disclosed embodiments, but, on the contrary, is intended to cover various modifications and equivalent arrangements included within the spirit and scope of the appended claims, and equivalents thereof. Accordingly, those of ordinary skill in the art will recognize that various changes and modifications of the exemplary embodiments described herein can be made without departing from the scope and spirit of the present disclosure, the disclosed embodiments, or the claimed embodiments.

The word "exemplary" is used herein to mean "serving as an example, instance, or illustration." Any embodiment described herein as "exemplary" is not necessarily to be construed as preferred or advantageous over other embodiments. Likewise, the term "embodiments" does not require that all embodiments include the discussed feature, advantage or mode of operation.

Unless otherwise defined herein, scientific and technical terms used in connection with the present disclosure shall have the meanings that are commonly understood by those of ordinary skill in the art. Nomenclatures used in connection with, and techniques described herein are those known and commonly used in the art. Also, descriptions of well-known functions and constructions are omitted for clarity and conciseness.

Throughout the text and claims, the terms "about" and "substantially" are used as terms of approximation, not terms of degree, and reflect the inherent variation associated with measurement, significant figures, and interchangeability, all as understood by a person having ordinary skill in the relevant art. Also, it is to be understood that throughout this disclosure and the accompanying claims, even values that are not preceded by the term "about" are also implicitly modified by that term, unless otherwise specified.

As used herein, the singular forms "a," "an," and "the" are intended to include the plural forms as well, unless the context clearly indicates otherwise. It will be further understood that the terms "comprises," "comprising," "includes," "including," "have" and/or "having" when used herein, specify the presence of stated features, integers, actions, steps, operations, elements, and/or components, but do not preclude the presence or addition of one or more other features, integers, actions, steps, operations, elements, components, and/or groups thereof.

To be suitable for use as an active pharmaceutical ingredient (API), the RHI produced should have a high purity and a low impurity profile, such as the RHI produced according to the methods disclosed herein, which can produce RHI API, in a solid form or in a liquid form, having a purity of 99.0% (w/w) or greater, a Total Impurity (not including the related substance desamido $Asn^{A21}$-RHI) of 0.8% or less, and impurity C of 0.1% (w/w) or less, all based on the total weight of the RHI API, in liquid or solid form, respectively. Also, the USP guidance on RHI specifies that the total impurities of RHI do not include the related substance desamido $Asn^{A21}$-RHI.

As used herein, "Total Impurity" or "Total Impurities" means all impurities in the RHI API except for the related substance desamido $Asn^{A21}$-RHI. Examples of the impurities included in the Total Impurity are the impurities provided in, but not limited to, Tables 1-2. In a preferred embodiment, the "Total Impurity" or "Total Impurities" does not include additional impurities that may generate and/or increase, as a function of time, after the RHI API is combined or formulated with other components, such as in a scenario where the RHI API is incorporated into a finished RHI drug product, such as an RHI aqueous solution for injection.

"Highly purified recombinant human insulin API" or "highly purified RHI API" means recombinant human insulin API, in a solid form or a liquid form, with a Total Impurity of 0.8% (w/w) or less based on the total weight of the RHI API, in solid or liquid form, respectively. For brevity herein, RHI API having a Total Impurity of 0.8% (w/w) or less based on the total weight of the RHI API, is deemed "highly purified RHI API." For example, RHI API (in solid form or liquid form) having a purity of 99.0% (w/w) or more, a Total Impurity of 0.8% (w/w) or less, and an impurity C of 0.1% (w/w) or less, based on the total weight of the RHI API, is deemed "highly purified RHI API."

Aspects of embodiments of the present disclosure include methods for reducing a difficult-to-remove impurity known as impurity C. Impurity C refers specifically to acetylated lysine at position 31 of the B-chain ($Lysine^{B31}$, $Lys^{B31}$, or $K^{B31}$) of RHI. Accordingly, as used herein, "impurity C" refers to a RHI bonded to an acetylated $Lys^{B31}$ wherein the acetylated $Lys^{B31}$ bonds to $Thr^{B30}$ on the B-chain. The $Lys^{B31}$ originates from the $Lys^{C1}$ of the C-peptide, as described herein. An acetylated $Lys^{B31}$ means that the $Lys^{B31}$ residue has an added group in (—CO—CH3), as illustrated below:

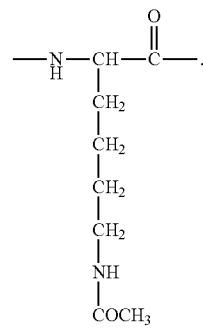

acetylated lysine residue

Impurity C is produced from an impurity C precursor during the processing of the single chain precursor (SCP) to RHI. The synthesis (e.g., processing) of RHI includes an immature form of RHI known as a single-chain precursor (SCP) molecule made of the A-chain polypeptide and the B-chain polypeptide with a C-peptide there-between. Various recombinant forms of the SCP molecule have utilized various lengths of the C-peptide, such as the SCP sequences having Formulae I, II, or III. SCP sequences known in the art include a C-peptide sequence from 1 amino acid residue to as many as 35 (or more) amino acid residues. One of the actions in the processing of RHI API from SCP is the cleavage and removal of the C-peptide from the A-chain and B-chain. However, to remove the C-peptide, enzyme cleavage actions are applied, which often produce additional impurities because of misdirected cleavages at sites susceptible to the particular enzyme. Accordingly, the difficult-to-remove impurities of RHI processing may vary according to the specific C-peptide sequence.

An impurity C precursor can be acetylated $Lysine^{C1}$ in the SCP. The impurity C precursor can be developed during the synthesis of the SCP, such as during the fermentation, gene expression, and/or inclusion body isolation of the SCP. Prior to the processing of SCP to RHI, the impurity C precursor can be as high as about 2-3% (w/w) in the SCP batch. Subsequently, impurity C is produced during enzymatic cleavage (e.g., enzymatic digestion) when processing the SCP into RHI. Thus, in some embodiments, in order for impurity C to be produced during enzymatic cleavage, a precursor to impurity C is developed during the synthesis of SCP, such as an acetylated Lysine$^{C1}$ in the SCP. Even after the application of several purification actions during the processing of the SCP to RHI, impurity C can still be as high as 0.7% (w/w) as an impurity in the final purified RHI API composition.

Impurity C may account for 0.5-0.7% (w/w) impurity in the final purified RHI API. Thus, the ability to produce highly purified RHI API, 99.0% (w/w) purity or above, and Total Impurities of 0.8% (w/w) or less, may be achieved if the amount of impurity C in the final purified RHI composition was lowered to 0.1% (w/w) or lower. One reason impurity C is difficult to remove is because it has an isoelectric point of about 5.40, which is similar to the isoelectric point of RHI and other impurities. Further, impurity C is difficult to remove because it is resistant to CPB enzyme digestion. Another reason impurity C is difficult to remove is that routine optimization of purification actions, as described in the Comparative Examples, were unable to significantly reduce the amount of the impurity C to 0.1% (w/w) or less based on the total weight of the RHI API. Therefore, a technical solution to removing or significantly reducing impurity C is needed.

Accordingly, the present disclosure solves this technical challenge by presenting methods for significantly reducing impurity C during the processing of the SCP into RHI. In particular, the disclosed methods significantly reduced the amount of the impurity C to 0.1% (w/w) or lower and Total Impurities to 0.8% (w/w) or less based on the total weight of the RHI API.

Embodiments of the present disclosure introduce methods for producing a solid form of RHI API having 99.0% (w/w) purity or greater and Total Impurities of 0.8% (w/w) or less based on the total weight of the RHI API in solid form. In particular, embodiments of the present disclosure include methods for reducing impurity C during the processing of SCP to RHI to 0.1% (w/w) or lower, which in turn results in the production of highly purified RHI API, in solid form, having 99.0% (w/w) purity or greater, and Total Impurities of 0.8% or less, based on the total weight of the RHI API in solid form.

Another difficult to remove impurity is Impurity E, which is Thr$^{B30}$ deletion-RHI. RHI API may have Impurity E at high concentrations, typically more than 0.3% (w/w). The disclosed methods can reduce Impurity E to less than 0.20% (w/w) as previously described. Impurity E can be produced during enzyme digestion, such as during enzyme cleavage actions 103 and 105 of method 100.

In some embodiments, the disclosed methods produced RHI API having a purity of about 99.0% (w/w), 99.1%, 99.2%, 99.3%, 99.4%, 99.5%, 99.6%, 99.7%, 99.8%, 99.9%, or more based on the total weight of the RHI API. In some embodiments, the disclosed methods produced RHI API having a Total Impurity of about 0.8% (w/w), 0.7%, 0.6%, 0.5%, 0.4%, 0.3%, 0.2%, 0.1% or less based on the total weight of the RHI API. In some embodiments, the disclosed methods reduced impurity C in RHI API to about 0.10% (w/w), 0.09%, 0.08%, 0.07%, 0.06%, 0.05%, 0.04%, 0.03%, 0.02%, 0.01%, or less based on the total weight of the RHI API.

"% (w/w)" denotes a percentage based on "weight per weight" or "weight by weight," as is customarily understood in the art. Throughout this disclosure, "%" is used synonymously and interchangeably with "% (w/w)." In the interest of brevity throughout this disclosure, when "(w/w)" is made in reference to an RHI (i.e. highly purified RHI API; RHI API; RHI; Lys$^{C1}$-RHI, and the like), it means that the "% (w/w)" or "%" is determined based on the weight of the component of interest divided by the total weight of the corresponding RHI. For example, RHI having a purity of 99.0%, or 99.0% (w/w), means that it has 99.0% RHI by weight (or mass) based on the total weight of the RHI, and 1.0% impurities by weight (or mass) based on the total weight of the RHI, wherein the 1.0% impurities by weight (or mass) includes the Total Impurities and the related substance desamido Asn$^{A21}$-RHI. Alternatively, RHI having impurity C of 0.1% means that it has 0.1% impurity C by weight (or mass) based on the total weight of the RHI, and the remaining 99.9% consists of RHI and other types of impurities (if any) by weight (or mass) based on the total weight of the RHI, such as the Total Impurities and desamido Asn$^{A21}$-RHI. Other types of impurities may include those listed in Tables 1 and 2.

Additionally, the purity or impurity percentages (w/w) can be assessed at different points in time within the disclosed methods with respect to the total weight of the particular components at that point in time. For example, the purity or impurity percentages (w/w) can be assessed after a column purification step. For instance, after action 109 of method 100, the amount of impurity C in Lys$^{C1}$-RHI is reduced to 0.1% (w/w) or less based on the total weight of the Lys$^{C1}$-RHI.

Human insulin is unmodified human insulin as it would exist in native human insulin. As known in the art, human insulin is a hormone that regulates glucose metabolism, and is made up of two polypeptide chains—an A-chain of 21 amino acids (SEQ ID NO: 1) and a B-chain of 30 amino acids (SEQ ID NO: 2) for a total of 51 amino acids. The A and B polypeptide chains are linked by disulfide bonds between A-chain cysteines paired with a respective B-chain cysteine. The disulfide bonds and corresponding cysteines (Cys) are Cys$^{A7}$-Cys$^{B7}$, Cys$^{A20}$-Cys$^{B19}$, and Cys$^{A6}$-Cys$^{A11}$. RHI is generally synthesized using recombinant DNA technology. The RHI produced according to the methods disclosed herein is RHI produced artificially. Throughout this disclosure, "human insulin" or "insulin" may be used interchangeably and synonymously with "recombinant human insulin" or "RHI."

As described herein, human insulin consists of two polypeptide chains, an A-chain of 21 amino acids, and a B-chain of 30 amino acids, a total of 51 amino acids, having three disulfide bonds between the cysteines (Cys) in Cys$^{A7}$-Cys$^{B7}$, Cys$^{A20}$-Cys$^{B19}$, and Cys$^{A6}$-Cys$^{A11}$, respectively. The B-chain of human insulin or RHI from $B_1$ to $B_{30}$ has the amino acid sequence FVNQHLCGSHLVEALYL-VCGERGFFYTPKT (SEQ ID NO: 2). The A-chain of human insulin or RHI from A1-A21 has the amino acid sequence GIVEQCCTSICSLYQLENYCN (SEQ ID NO: 1).

An "amino acid residue" or "residue" means an amino acid in which a hydroxyl group (i.e. OH) has been removed from a carboxy group (i.e. COOH), and/or a hydrogen atom (i.e. H$^+$) has been removed from an amino group (i.e. NH$_2$).

As used herein, "cleavage" "digestion," "enzymatic cleavage," "enzymatic digestion," "cleaving," "digesting," "enzyme-cleaving" and like terms refer to the disruption of bonds between amino acids in a peptide chain carried out by an enzyme (e.g., carboxypeptidase B (CPB) or trypsin).

RHI is synthesized using a single chain precursor (SCP) molecule commonly known as a preproinsulin. "SCP" is used interchangeably and synonymously with the term "preproinsulin." An SCP typically includes a leader peptide sequence, an A-chain having 21 amino acids, a B-chain having 30 amino acids, and a C-peptide made of 1-35 (or more) amino acids connecting the A-chain and the B-chain. The leader peptide sequence may also be referred to as the signal peptide. An SCP may be synthesized using any suitable series of actions comprising gene expression, fermentation, inclusion body isolation, solubilization, and sulfonation. Commonly used master host cells for SCP synthesis include *Escherichia coli* (*E. coli*), yeast, *Bacillus subtilis, Salmonella* or other modified strains that are suitable for recombinant protein expression. Thus, the SCP in embodiments of the present disclosure may be produced by any suitable means known in the art. In some embodiments of the present disclosure, the SCP is synthesized using the techniques disclosed in Ferring. See European Patent No. EP0871474B1, entitled "Generation of Human Insulin," filed Dec. 29, 1994, and granted Mar. 1, 2007, the entire contents of which are incorporated herein by reference. In some embodiments of the present disclosure, the SCP is synthesized using *E. coli* as the master host cell. In other embodiments of the present disclosure, the SCP is synthesized using yeast as the master host cell.

In some embodiments of the present disclosure, the SCP has a C-peptide made of 2 amino acids, Arginine as $X_{C2}$ and Lysine as $X_{C1}$ (SEQ ID NO: 3), in which the $Arg^{C2}$ connects to (binds to) $Gly^{A1}$ of the A-chain, and the $Lys^{C1}$ connects to $Thr^{B30}$ of the B-chain. The amino acid abbreviations, such as "Arg" or "R" for Arginine and "Lys" or "K" for Lysine, are well-known in the art and in the interest of brevity, do not need to be detailed herein. Typically, the C-peptide is a long peptide chain of about 32 amino acids or more. However, in a preferred embodiment, the C-peptide is a short peptide chain consisting of 2 amino acids, $Arg^{C2}$-$Lys^{C1}$. In such case, when the $Arg^{C2}$-$Lys^{C1}$-RHI is enzyme-cleaved to produce $Lys^{C1}$-RHI and an Impurity C, the C-peptide is essentially cleaved in half.

In other embodiments, the C-peptide comprises the $Lys^{C1}$, the $Arg^{C2}$, and an Arg as a last residue of the C-peptide that bonds to $Gly^{A1}$ of the A-chain. In still other embodiments, the C-peptide is a short peptide chain comprising the $Lys^{C1}$, the $Arg^{C2}$, and an Arg as a last residue of the C-peptide that bonds to $Gly^{A1}$ of the A-chain, in which the short peptide chain consists of 10 amino acids or less, including 9 amino acids, 8 amino acids, 7 amino acids, 6 amino acids, 5 amino acids, 4 amino acids, 3 amino acids, or 2 amino acids.

In some embodiments, the SCP molecule is represented by Formula I:

$$(X_n\text{-}X_{C\text{-}term})\text{-}(X_{B1}\text{-}X_{B30})\text{-}(X_{C1}\text{-}X_{C2})\text{-}(X_{A1}\text{-}X_{A21}). \quad \text{Formula I}$$

With reference to Formula I, $X_n$-$X_{C\text{-}term}$ is a leader peptide sequence, wherein:

$X_{C\text{-}term}$ is the C-terminal residue of the leader peptide that bonds with $Phe^{B1}$ of the B-chain, and $X_n$ denotes any number of amino acids suitable for use together with $X_{C\text{-}term}$ as a leader peptide sequence. In some embodiments, $X_n$-$X_{C\text{-}term}$ is at least 1, 2, 3, 4, and up to 40, 50, 60, 70 (or more) amino acids. In some embodiment $X_{C\text{-}term}$ is Arginine.

With reference to Formula I, $X_{B1}$-$X_{B30}$ is the B-chain of native human insulin from amino acid residue 1 to 30 of the B chain having the amino acid sequence FVNQHLCGSHLVEALYLVCGERGFFYTPKT (SEQ ID NO: 2).

```
                                        (SEQ ID NO: 2)
FVNQHLCGSHLVEALYLVCGERGFFYTPKT.
```

With reference to Formula I, $X_{C1}$-$X_{C2}$ is a C-peptide wherein:

$X_{C1}$ is Lysine ($Lys^{C1}$), and $Lys^{C1}$ bonds with $Thr^{B30}$ of the B-chain, $X_{C2}$ is Arginine ($Arg^{C2}$), and $Arg^{C2}$ bonds with $Gly^{A1}$ of the A-chain, thus C-peptide has an amino acid sequence of KR (SEQ ID NO: 3).

With reference to Formula I, $X_{A1}$-$X_{A21}$ is the A-chain of native human insulin from amino acid residue 1 to 21 of the A-chain having the amino acid sequence GIVEQCCTSICSLYQLENYCN (SEQ ID NO: 1).

In some embodiments of the present disclosure, an SCP according to Formula I includes the leader peptide sequence $X_n$-$X_{C\text{-}term}$ having $AX_mR$, in which the carboxyl terminal of the R connects to $Phe^{B1}$ of the B-chain, and $X_m$ is any suitable number of amino acids, such as 1, 2, 3, 4, and up to 40, 50, 60, or 70 amino acids.

Therefore, an exemplary embodiment of an SCP according to Formula I has the amino acid sequence of:

```
                                        (SEQ ID NO: 6)
5'AX_mR-FVNQHLCGSHLVEALYLVCGERGFFYTPKT-KR-

GIVEQCCTSICSLYQLENYCN 3'
```

In some embodiments of the present disclosure, SCP is represented by Formula II:

$$(X_n\text{-}X_{C\text{-}term})\text{-}(X_{B1}\text{-}X_{B30})\text{-}(X_{C1}\text{-}X_{C2}\text{-}X_{C\text{-}term})\text{-}(X_{A1}\text{-}X_{A21}). \quad \text{Formula II}$$

With reference to Formula II, $X_n$-$X_{C\text{-}term}$ is a leader peptide sequence, wherein:

$X_{C\text{-}term}$ is the C-terminal residue of the leader peptide that bonds with $Phe^{B1}$ of the B-chain, $X_n$ denotes any number of amino acids suitable for use as a leader peptide sequence. In some embodiments, $X_n$-$X_{C\text{-}term}$ is at least 1, 2, 3, 4, and up to 40, 50, 60, 70 amino acids. In some embodiment $X_{C\text{-}term}$ is Arginine.

With reference to Formula II, $X_{B1}$-$X_{B30}$ is the B-chain of native human insulin from amino acid residue 1 to 30 of the B chain having the amino acid sequence

```
                                        (SEQ ID NO: 2)
FVNQHLCGSHLVEALYLVCGERGFFYTPKT.
```

With reference to Formula II, $X_{C1}$-$X_{C2}$-$X_{C\text{-}term}$ is a C-peptide, wherein:

$X_{C1}$ is Lysine ($Lys^{C1}$), $Lys^{C1}$ bonds with $Thr^{B30}$ of the B-chain, $X_{C2}$ is Arginine ($Arg^{C2}$)

$X_{C\text{-}term}$ is Arginine ($Arg^{C3}$), $Arg^{C3}$ that bonds with $Gly^{A1}$ of the A-chain.

With reference to Formula II, $X_{A1}$-$X_{A21}$ is the A-chain of native human insulin from amino acid residue 1 to 21 of the A-chain having the amino acid sequence GIVEQCCTSICSLYQLENYCN (SEQ ID NO: 1).

In some embodiments, the SCP according to Formula II, the leader peptide sequence $X_n$ includes at least $AX_mR$ as defined above, in which the carboxyl terminal of the $Arg^{Xn}$ connects to $Phe^{B1}$ of the B-chain, and $X_{C1}$-$X_{C2}$-$X_{C\text{-}term}$ is KRR (SEQ ID NO: 4). Therefore, an exemplary embodiment of an SCP according to Formula II has the amino acid sequence of:

(SEQ ID NO: 7)
5'AX$_m$R-FVNQHLCGSHLVEALYLVCGERGFFYTPKT-KRR-

GIVEQCCTSICSLYQLENYCN 3'

In some embodiments, the SCP may be represented by Formula III:

$$(X_n\text{-}X_{C\text{-}term})\text{-}(X_{B1}\text{-}X_{B30})\text{-}(KR—X_{Cn}\text{-}R)\text{-}(X_{A1}\text{-}X_{A21}),$$ Formula III wherein in Formula III, a C-peptide is represented by KR-$X_{Cn}$-R, wherein $X_{Cn}$ represents any suitable number of amino acids, such as up to 32 amino acids or more, which may include any amino acid except for Lysine, and all other variables are as defined in Formulae I and II. In some embodiments, KR-$X_{Cn}$-R is KRQGR (SEQ ID NO: 5), wherein the C-peptide comprises a $Lys^{C1}$, an $Arg^{C2}$, and an Arg as a last residue of the C-peptide that bonds to $Gly^{A1}$ of the A-chain. Therefore, an exemplary embodiment of an SCP according to Formula II has the amino acid sequence of:

(SEQ ID NO: 8)
5'AX$_m$R-FVNQHLCGSHLVEALYLVCGERGFFYTPKT-KRQGR-GIVEQCCTSICSLYQLENYCN 3'

In some embodiments of Formulae I, II, or III, the SCP further includes a precursor to impurity C, such as an acetylated $Lysine^{C1}$ in the C-peptide, or any other precursor that can result in impurity C. As discussed, the impurity C precursor can develop during SCP synthesis.

Embodiments of the present disclosure include synthesizing the SCP following any suitable method expression or synthesizing technique. After synthesis, action the SCP (i.e., preproinsulin) may be processed to remove (e.g., by enzymatic cleavage) the leader peptide to produce proinsulin. In some embodiments preproinsulin is digested with trypsin, to remove the leader peptide sequence. Following removal of the leader peptide, the proinsulin has the A-chain, the B-chain, and the C-peptide, as shown in FIG. 2A. Accordingly, additional purification and enzyme cleavage actions are applied to convert the proinsulin to RHI by removing the C-peptide and impurities.

Methods of Producing Highly Purified RHI API Having Purity of 99.0% or More, Total Impurity of 0.8% or Less, and Impurity C of 0.1% or Less.

Embodiments of the present disclosure are directed to methods for processing the SCP into a highly purified RHI API, with 99.0% (w/w) purity or greater, a Total Impurity of 0.8% (w/w) or less, and an amount of impurity C of 0.1% (w/w) or less, based on the total weight of the RHI API. In a preferred embodiment, the highly purified RHI API is in a solid form. In other embodiments, the highly purified RHI API is in a liquid form, such as in an aqueous form.

In some embodiments, the method 100 as presented in FIG. 1 includes actions 101, 102, 103, 104, 105, 106, 107, 108, 109, 110, and 111 as shown, for purifying RHI with 99.0% (or more) (w/w) purity based on the total weight of the RHI API. The method 100 begins with an SCP having Formulae I, II, or III. In this exemplary embodiment of method 100, the SCP sequence has Formula I, which has a short C-peptide sequence of only two amino acids, $Arg^{C2}$-$Lys^{C1}$ (denoted in SEQ ID NO: 3).

At action 101, the SCP is refolded using refolding buffers, which are known in the art. Action 101 refolds the SCP to form the proper disulfide bonds that are present in native human insulin and RHI (e.g., $Cys^{A7}$-$Cys^{B7}$, $Cys^{A20}$-$Cys^{B19}$, and $Cys^{A6}$-$Cys^{A11}$, respectively) as shown in FIG. 2A.

At action 102, a Lysine protecting group, (e.g., citraconic anhydride, tert-Butyloxycarbonyl (Boc), Benzyloxycarbonyl (Cbz, Z), or Allyloxycarbonyl (Alloc)), is applied to the preproinsulin to protect the two Lysine residues present in the proinsulin. In this exemplary embodiment, Lysine residues of the proinsulin protein are present at $Lys^{C1}$ of the C-peptide and $Lys^{B29}$ of the B-chain. FIG. 2A shows the protected $Lys^{C1}$ and $Lys^{B29}$ in the refolded proinsulin (SEQ ID NO: 6).

Action 103 is a first enzyme cleavage action. In this exemplary embodiment of method 100, trypsin is applied to the proinsulin. As shown in FIGS. 2B-2C, trypsin cleaves: (i) the peptide bond between $Arg^{R1}$ of the leader peptide sequence and $Phe^{B1}$ of the B-chain, resulting in a [(B-Chain)-(C-peptide)-(A-Chain)] polypeptide (SEQ ID NO: 9), and (ii) the peptide bond between $Gly^{A1}$ of A-chain to $Arg^{C2}$ of the C-peptide, resulting in the A-chain (SEQ ID NO: 1) and a peptide fragment encompassing $Phe^{B1}$ to $Thy^{B30}$ and $Lys^{C1}$-$Arg^{C2}$ (SEQ ID NO: 10), which are linked via the RHI disulfide bonds as described above. Thus, after this first enzyme-cleaving (i.e., enzyme digestion) action, $Arg^{R1}$ is no longer bonded to $Phe^{B1}$ and $Gly^{A1}$ is no longer bonded to $Arg^{C2}$, as shown in FIGS. 2B-2C. Even though $Gly^{A1}$ is no longer bonded to $Arg^{C2}$, the A-chain is still bonded to the B-chain because of the disulfide bonds formed at $Cys^{A7}$-$Cys^{B7}$ and $Cys^{A20}$-$Cys^{B19}$, as also shown in FIGS. 2B-2C. FIG. 2D depicts the proinsulin at the conclusion of action 103. Also shown in FIG. 2D, $Lys^{C1}$ and $Lys^{B29}$ of the proinsulin are still protected by the Lysine protecting group.

At action 104, the first column purification action utilizes anion-exchange column chromatography to separate the cleaved leader peptide sequence from the $Arg^{C2}$-$Lys^{C1}$-RHI. The terms "$Arg^{C2}$-$Lys^{C1}$-RHI," "Arg(C2)-Lys(C1)-RHI," "Arg-Lys-RHI," "Arg-Lys-insulin" and "Arg-Lys-RHI" each have the same meaning and are used interchangeably herein to refer to human insulin A-chain and B-chain with a C-peptide of Arginine at position 2 ($X_{C2}$) and Lysine at position 1 ($X_{C1}$) in Formulae I and II. Other impurities may also be separated or reduced at action 104. Column chromatography, such as anion-exchange column chromatography, is known in the art for the separation of a protein of interest from the solution mixture, and/or to reduce impurities relative to the protein of interest.

In an anion-exchange column chromatography, the ion-exchange resin contains positively-charged groups (i.e. cations), which in turn will bind to negatively-charged molecules. An anion-exchange column chromatography may be performed at a higher pH level, and in particular, at a pH above the isoelectric point of the peptide of interest so that the protein of interest has a negative charge and will bind to the positively-charged resin. Accordingly, at the end of action 104, the batch continuing onto the next actions includes primarily Arg-Lys-RHI and impurities.

Action 105 includes a second enzyme-cleaving action. At action 105, carboxypeptidase B (CPB) is applied to the Arg-Lys-RHI. CPB is particularly effective in enzyme-cleaving the peptide bonds of basic amino acids such as Arginine and Lysine. At action 105, in some embodiments, CPB having a concentration of about 1/10000 of protein (w/w) is applied to the Arg-Lys-RHI. At action 105, in some embodiments, CPB can be applied at a pH having a range of about 7.0 to about 10.0, about 7.0 to about 8.0, about 7.5 to about 8.5, about 8.0 to about 9.0, about 8.5 to about 9.5, or about 9.0 to about 10.0. At action 105, in some embodiments, CPB can be applied at a temperature in the range of about 22 to about 28° Celsius, about 23 to about 27° Celsius, or about 24 to about 26° Celsius. At action 105, in some embodiments, CPB can be applied for at least about 1, 2, 3, 4, 5, 6, or more hours.

Figure 2A:
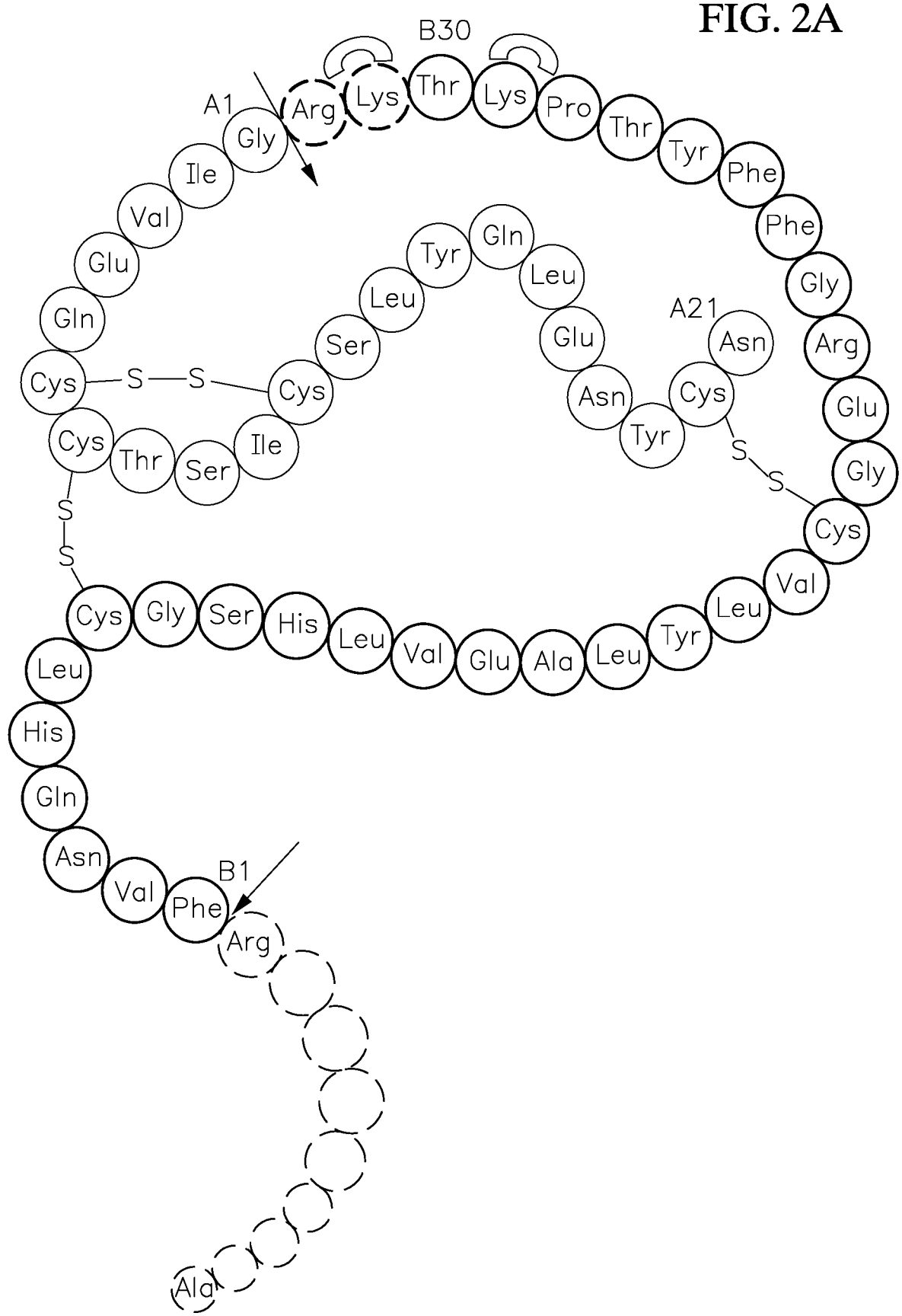
FIG. 2, which includes FIGS. 2A (SEQ ID NO: 6), 2B (SEQ ID NO: 9), 2C (SEQ ID NOS: 1 and 10), 2D (SEQ ID NOS: 1 and 10), 2E (SEQ ID NOS: 1 and 11), 2F (SEQ ID NOS: 1 and 11), 2G (SEQ ID NOS: 1 and 2), and 2H (SEQ ID NOS: 1 and 2), depicts the processing of SCP and proinsulin into highly purified RHI API according to embodiments of the present disclosure.
Figure 2B:
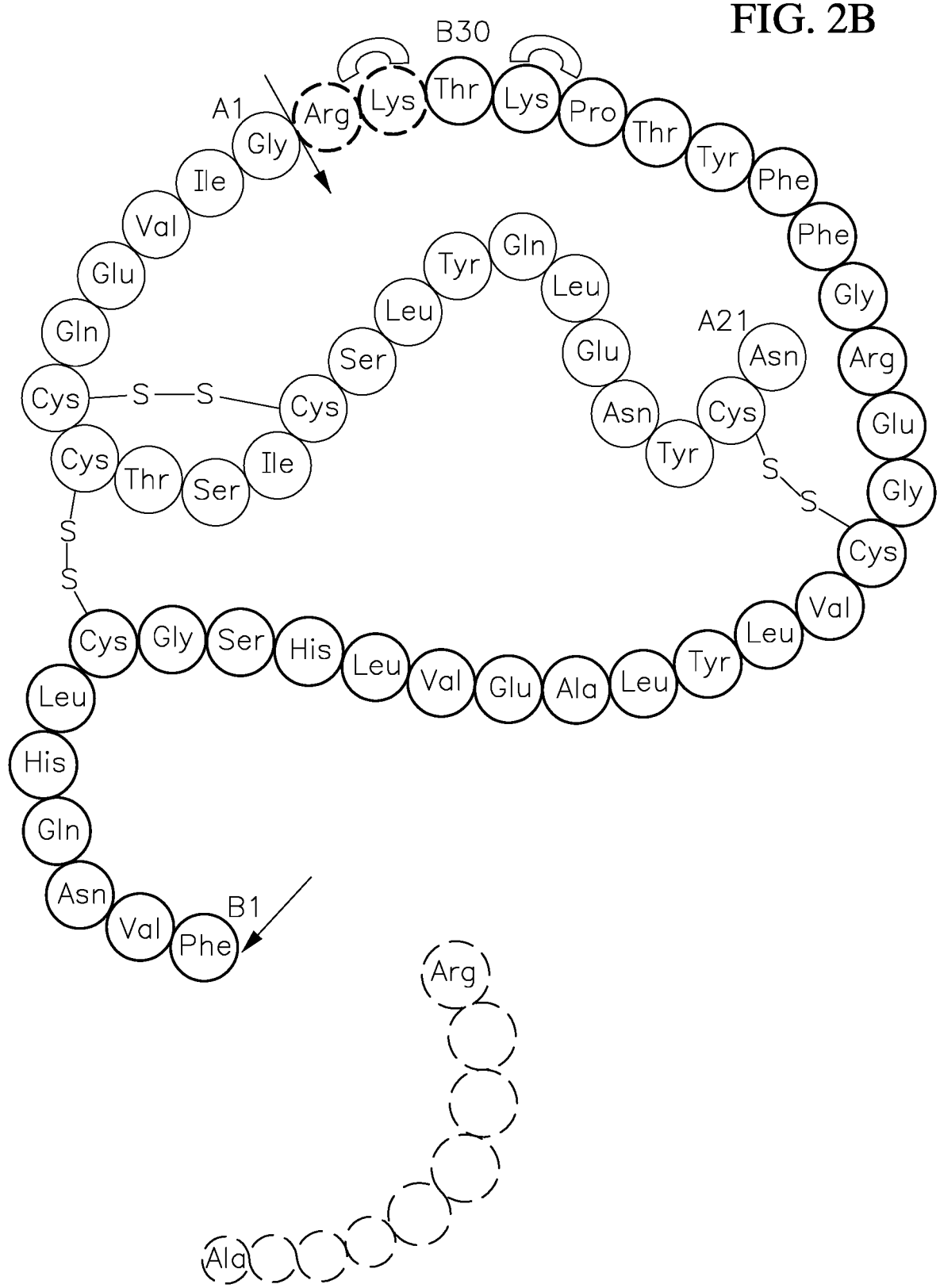
Figure 2C:
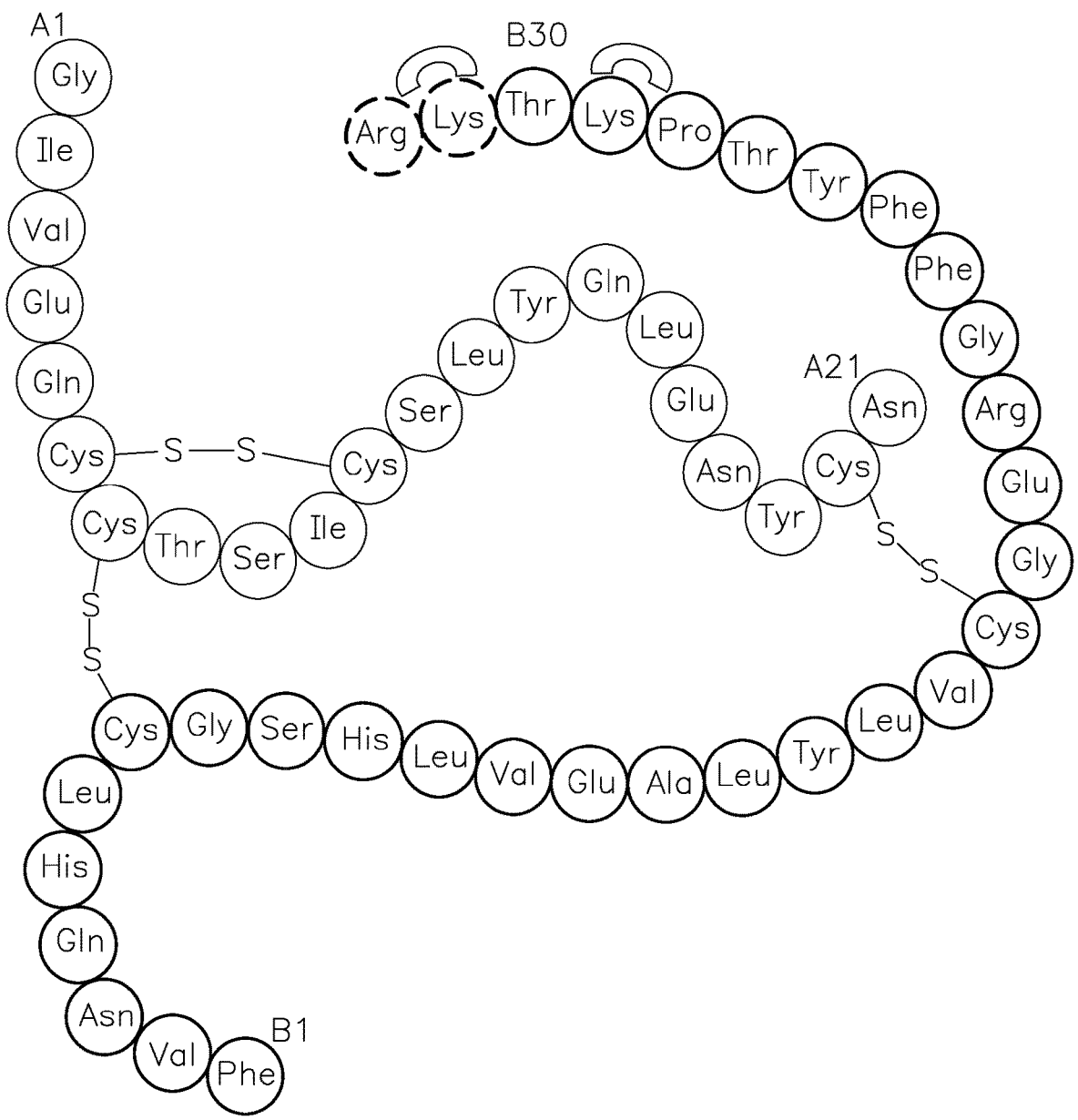
Figure 2D:
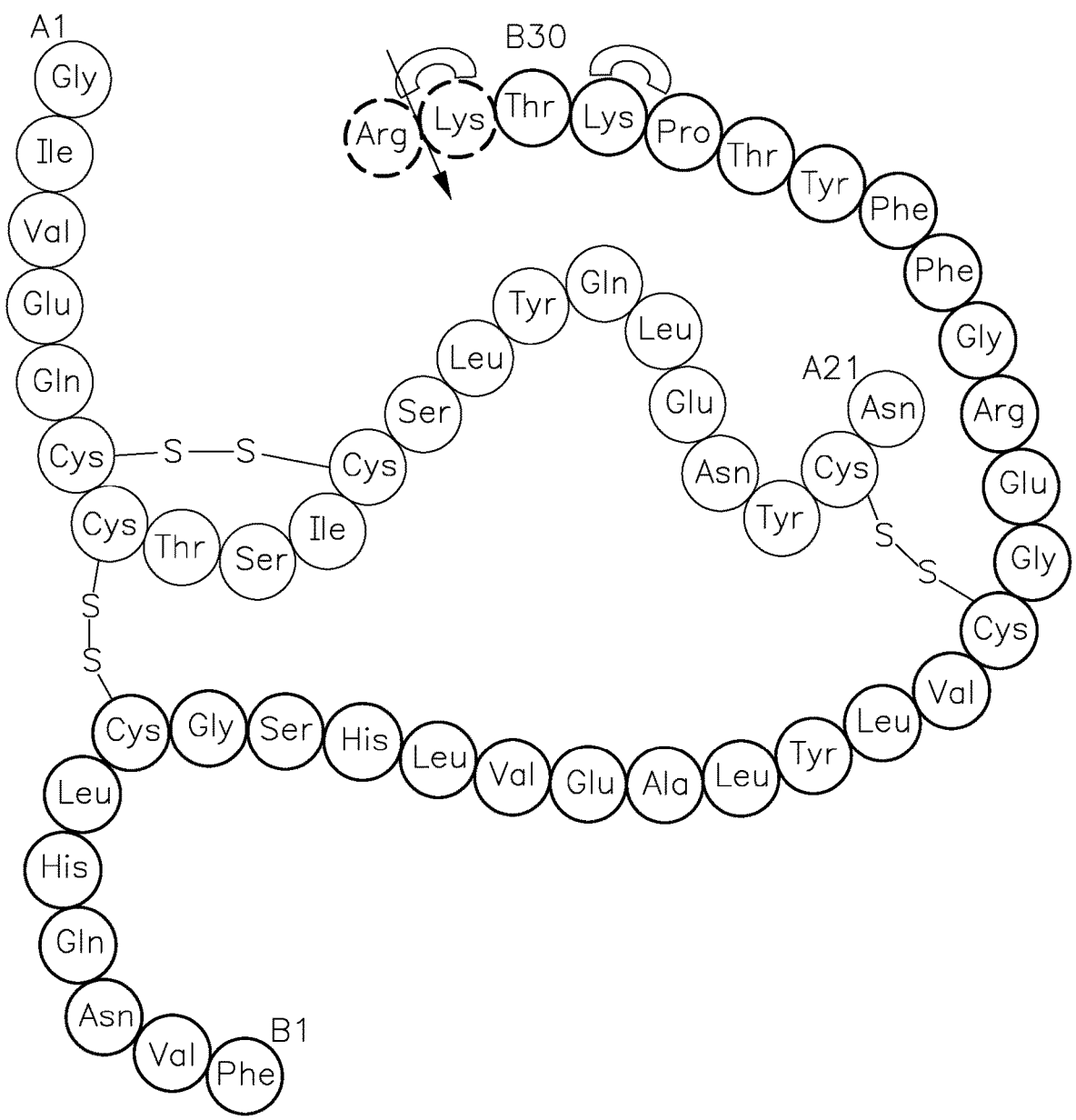
Figure 2E:
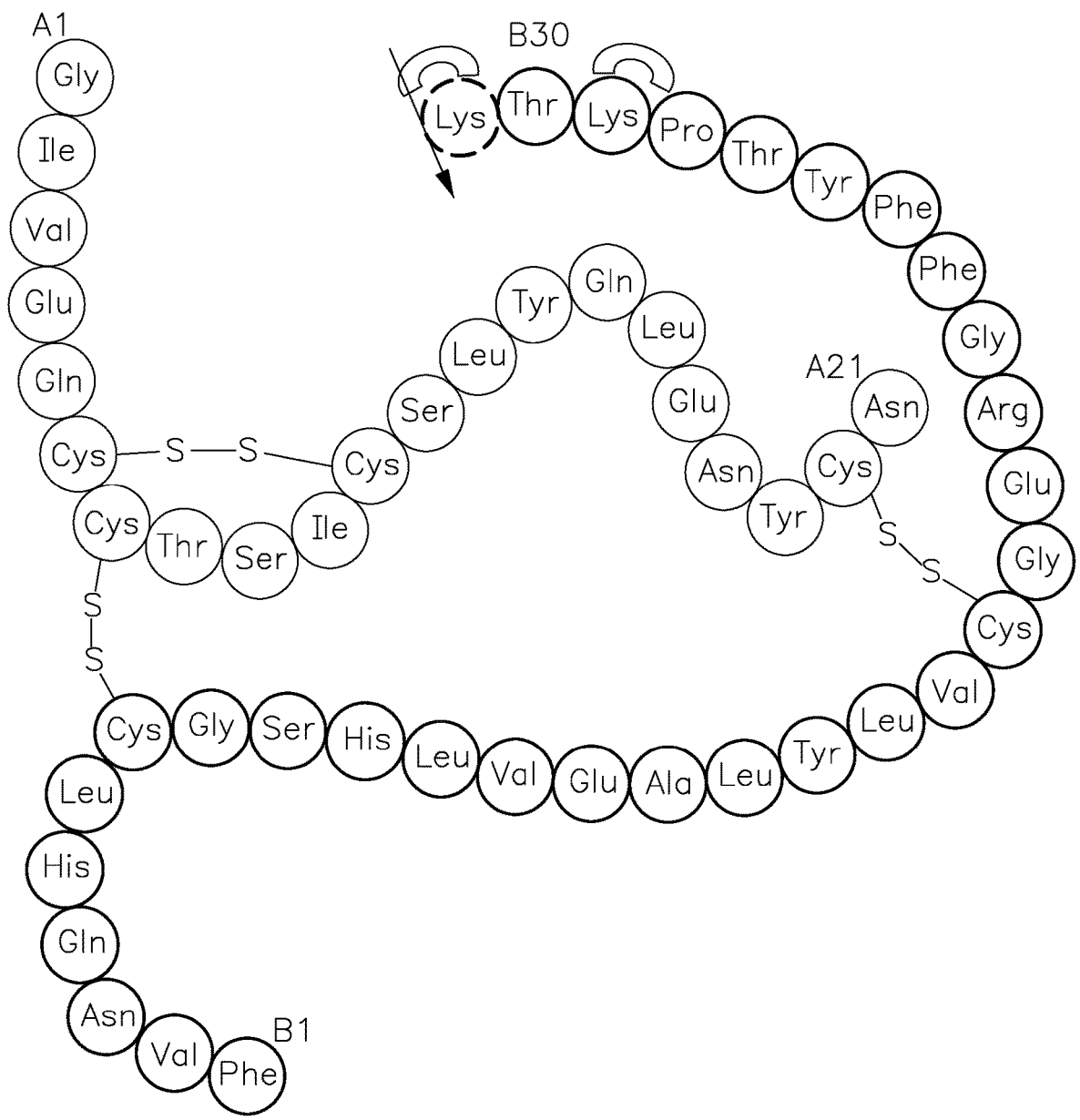

As shown in FIG. 2E, because the Lysine residue at ($X_{C1}$) is still protected, CPB only cleaves the peptide bond between $Arg^{C2}$ and $Lys^{C1}$, thereby resulting in $Lys^{C1}$-RHI and unbound $Arg^{C2}$. In embodiments where the C-peptide is a short peptide consisting of $Arg^{C2}$-$Lys^{C1}$ only (SEQ ID NO: 3), then this enzyme-cleaving action 105 essentially cleaves the C-peptide in half. Subsequently, the unbound $Arg^{C2}$ may be removed at action 108 as described below, resulting in the A-chain (SEQ ID NO: 1) and a peptide fragment encompassing $Phe^{B1}$ to $Thy^{B30}$ and $Lys^{C1}$ (SEQ ID NO: 11), which are linked via the RHI disulfide bonds as described above. "$Lys^{C1}$-RHI," "Lys(C1)-RHI," "Lys-RHI," "Lys-insulin," and "Lys-RHI" each have the same meaning and are used interchangeably herein to refer to human insulin of A-chain and B-chain polypeptides with Lysine of the C-peptide bonded to the Threonine at position 30 of the B chain ($Thr^{B30}$) after $Arg^{C2}$ has been cleaved from the Arg-Lys-RHI.

With reference to action 105, the result of adding CPB to the Arg-Lys peptide is the production of impurity C. With impurity C produced in action 105, the technical challenge was removing impurity C from Lys-RHI.

With continued reference to action 105, because the C-peptide has only two amino acid residues, this effectively cuts the C-peptide in half, as shown in FIG. 2E. This is a deviation from the protocols in which the C-peptide has been cleaved in full in a single enzyme cleavage action. The motivation to cleave the full C-peptide (e.g., both or all amino acids) in a single enzyme cleavage action is to avoid additional impurities caused by multiple enzyme actions, which would be contrary to the goal of producing highly purified RHI. Moreover, additional impurities would require additional purification actions, which reduce yield and further complicate the overall manufacturing process. Therefore, previous protocols have cleaved the full C-peptide with one digestion action.

While the present disclosure and methods according to embodiments of the present disclosure are not bound by any specific theory, the methods (e.g., 100) for enzyme-cleaving a C-peptide using an additional enzyme digestion action 105 in combination with action 109, unexpectedly produced a RHI API having an amount of impurity C of 0.1% (w/w) or less, which enabled the production of highly purified RHI API, in a solid form, having a purity of 99.0% (w/w) or greater and a Total Impurity of 0.8% (w/w) or less, based on the total weight of the RHI API in solid form. According to embodiments of the present disclosure, by increasing the number of enzyme-cleaving actions, it is possible to lower the amount of impurity C to 0.1% (w/w) or less in the RHI API.

Figure 2F:
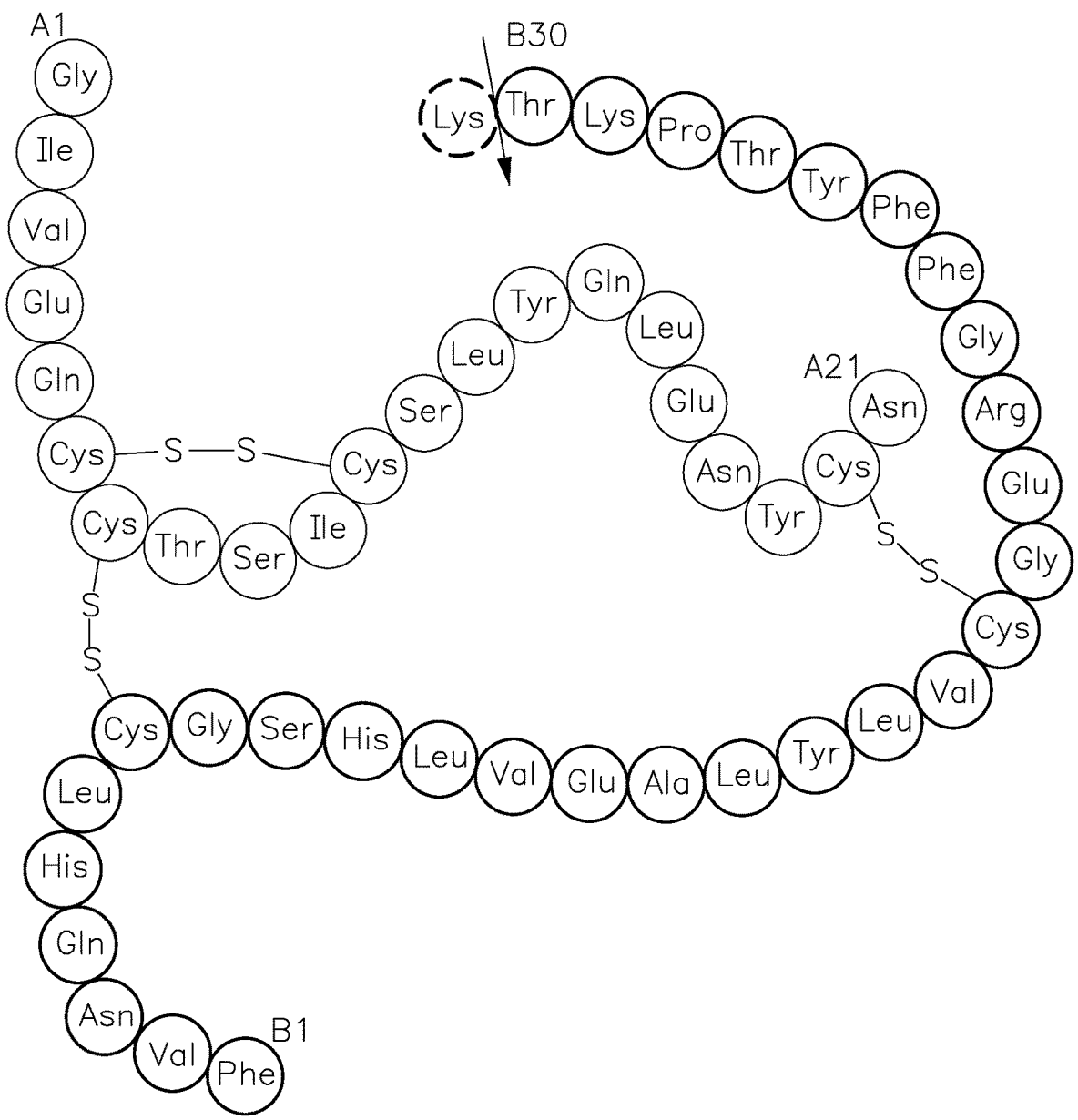

With reference to action 106, the Lysine residues at $Lys^{C1}$ and $Lys^{B29}$ in the Lys-RHI are de-protected by removing the Lysine protecting group. Thus, as demonstrated in FIG. 2F, the Lysine residues at $Lys^{C1}$ and $Lys^{B29}$ in the Lys-RHI are now susceptible of being cleaved by enzymatic digestion.

In some embodiments, with reference to action 107, aprotinin may be optionally applied to the de-protected Lys-RHI to remove the trypsin leftover from action 103.

Action 108 is a second column purification action, which utilizes anion-exchange column chromatography to separate the $Arg^{C2}$ and other impurities from the Lys-RHI based on their charge. At action 108, the one or more impurities separated may include those commonly known in the art as well as the impurities identified herein, including the impurities identified in the Tables 1-6. Note that the separation of impurities may include the type of impurities, the amount of the impurities, or the combination thereof. In some embodiments, at action 108, anion-exchange column chromatography is performed using a pH in the range of 7.0 to 9.5, or any range subsumed therein, including but not limited to 7.0 to 9.0, 7.0 to 8.5, 7.0 to 8.0, 7.0 to 7.5, 7.5 to 9.0, 7.5 to 8.5, 7.5 to 8.0, 8.0 to 9.5, 8.0 to 9.0, or 8.0 to 8.5. In others embodiments, at action 108, anion-exchange column chromatography is performed using a pH in the range of about 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4 or 9.5

At the end of action 108, the batch continuing onto the next actions contains primarily Lys-RHI and impurities not removed in action 108, such as impurity C.

Action 109 is a third column purification action. Prior to action 109, the batch has NMT (no more than) 20% (w/w) impurities. Action 109 utilizes reverse phase high performance liquid chromatography (RP-HPLC) utilizing a C18 phase column. Note that other phase column sizes can also be utilized at action 109, such as a C8 phase column. In some embodiments, the RP-HPLC may further include a semi-preparation column, a preparation column, or a combination thereof. In some embodiments, the semi-preparation column is a column having a length of about 250 mm and an internal diameter of about 10.0 mm, as shown in Table 1. In some embodiments, the preparation column is a column having a length of about 250 mm and an internal diameter of about 21.20 mm. In still other embodiments, the preparation column is a column having a length of about 350 mm and an internal diameter of about 100 mm. The C18 phase column can utilize a particle size of 3 μm to 50 μm (or any range subsumed therein), such as 3 μm, 5 μm, 10 μm, 15 μm, 20 μm, 25 μm, 30 μm, 35 μm, 40 μm, 45 μm, or 50 um.

At action 109, this C18 phase column and RP-HPLC process is used to separate impurity C and other impurities from Lys-RHI on the basis of their respective hydrophobicity. At action 109, in some embodiments, the column chromatography is performed using mixtures of water or aqueous buffers such as $(NH_4)_2SO_4$ and organic solvents such as isopropyl (IPA) as mobile phase. At action 109, in some embodiments, the column chromatography is performed using a pH in the range of about 1.5 to about 3.5 or any range subsumed therein, including but not limited to, about 2.0 to about 3.0, about 2.5 to about 3.0, about 3.0 to about 3.5, about 2.2 to about 2.8, or about 2.5 to about 3.0. In some embodiments, at action 109, column chromatography is performed using a pH of about 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, or 3.5. Other impurities may also be separated or reduced at action 109.

At the end of action 109, the batch continuing onto the next actions contains primarily Lys-RHI with impurity C (acetylated Lys-RHI) at about 0.10% (w/w) or less. This column purification action 109 in combination with the enzyme digestion action 105, unexpectedly produced Lys-RHI with 0.1% (w/w) or less impurity C based on the total weight of Lys-RHI, which in turn, ultimately produces highly purified RHI API having impurity C of 0.1% (w/w) or less based on the total weight of the highly purified RHI API.

The process of RP-HPLC may include any suitable silica-based resin. A non-limiting example of a silica-based resin for RP-HPLC includes C18 resin, which includes 18 carbon atoms as the stationary phase. In some embodiments, other size carbon molecules may also be used in the column, such as C4 (4 carbon atoms), C5 (5 carbons), C6 (6 carbon atoms), C8 (8 carbon atoms), C12 (12 carbon atoms), C16 (16 carbon atoms), C18 (18 carbon atoms), and C20 (20 carbon atoms). In addition to carbon-bonded silica, pure silica, cyano-bonded silica, phenyl-bonded silica, and other suitable silica may be used in the RP-HPLC.

In other embodiments, the RP-HPLC has an internal diameter of about 50 mm, 100 mm, 200 mm, 300 mm, 400 mm, 500 mm, 600 mm, or more, depending on the scale needs of the commercial production of the RHI API. In still other embodiments, the RP-HPLC has a column length of about 200 mm, 250 mm, 300 mm, 350 mm, 400 mm, 450 mm, 500 mm, 550 mm, 600 mm, or more, depending on the scale needs of the commercial production of the RHI API.

Figure 2G:
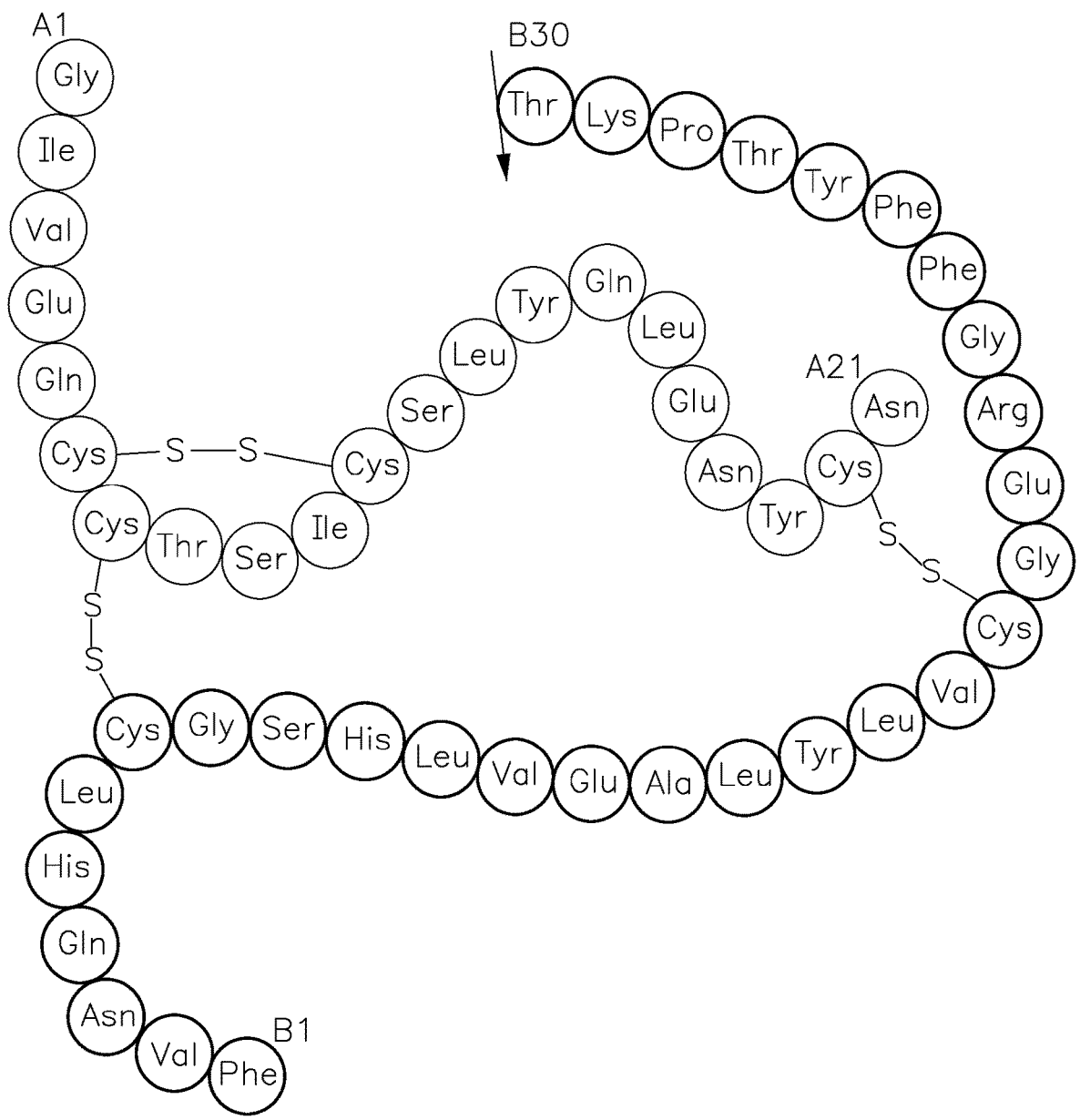
Figure 2H:
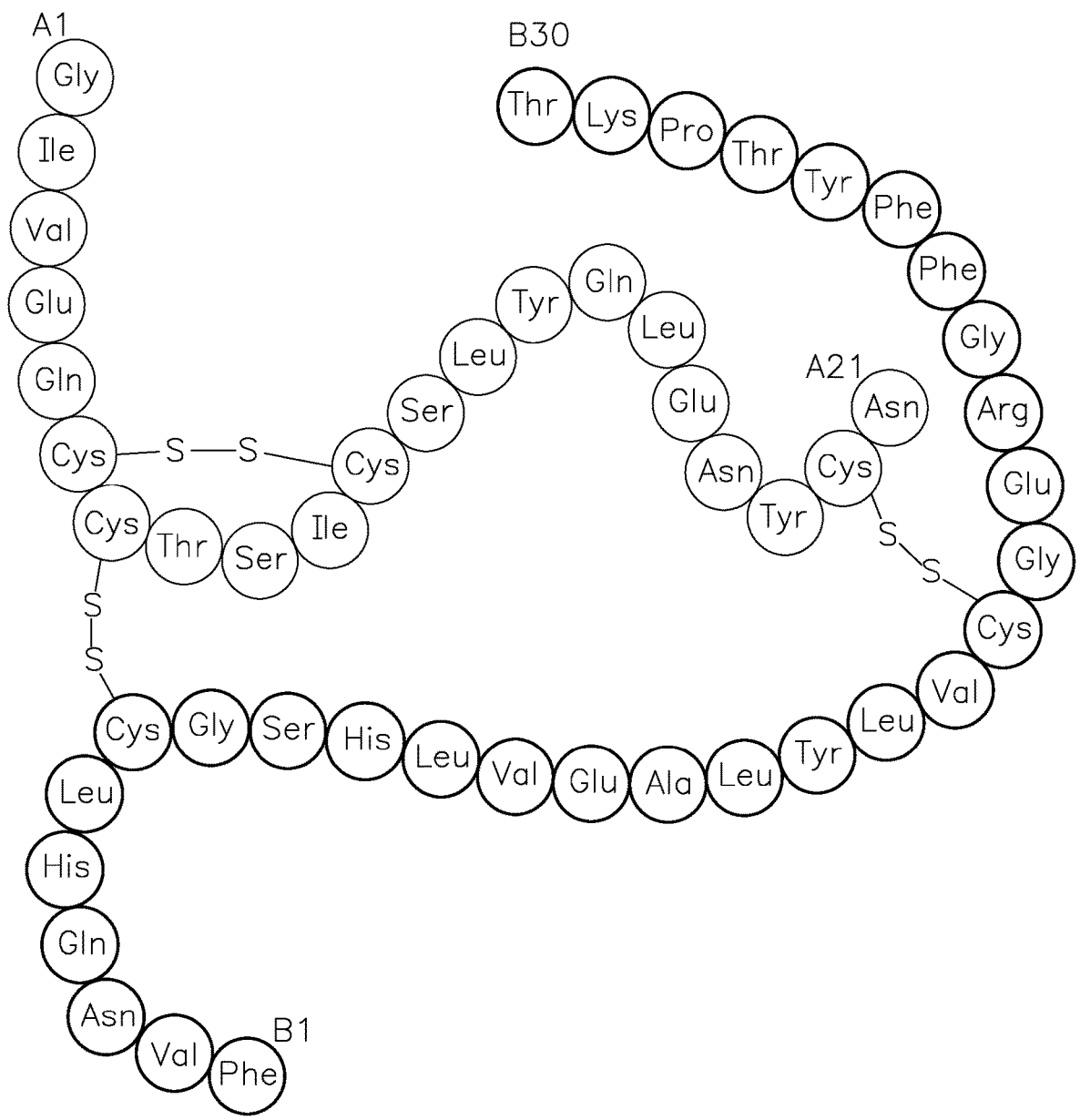

Action 110 is a third enzyme-cleaving action. At action 110, because Lys is no longer protected, CPB is capable of enzyme-cleaving the peptide bond between $Lys^{C1}$ and $Thr^{B30}$, as depicted in FIG. 2G, thereby removing the C-peptide ($Lys^{C1}$ residue) from the B-chain, and producing RHI with the A-chain (SEQ ID NO: 1) and the B-chain (SEQ ID NO: 2). At the conclusion of action 110, the RHI is shown in FIG. 2H. Optionally, at action 110, RP-HPLC can be diluted with water to further reduce Impurity E. For example, RP-HPLC can be diluted 2×, 3×, 4×, or more, which in turn, reduces Impurity E, as shown in Example 9.

Action 111 is a fourth column purification action. Action 111 utilizes reverse phase high performance liquid chromatography (RP-HPLC) utilizing a C18 column to remove $Lys^{C1}$ and other impurities to produce highly purified RHI having a Total Impurity of 0.8% (w/w) or less. At action 111, the one or more impurities separated may include those commonly known in the art as well as the impurities identified herein, including the impurities identified in the Tables 1-6. Note that the separation of impurities may include the type of impurities, the amount of the impurities, or the combination thereof. Note that other phase column sizes can also be utilized at action 111, such as a C8 phase column. In some embodiments, at action 111, RP-HPLC is performed using a pH in the range of about 1.5 to about 3.5 or any range subsumed therein, including but not limited to, about 2.0 to about 3.0, about 2.5 to about 3.0, about 3.0 to about 3.5, about 2.2 to about 2.8, or about 2.5 to about 3.0. In some embodiments, at action 109, column chromatography is performed using a pH of about 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, or 3.5. At the end of action 111, highly purified RHI, in liquid form, is produced and is suitable for use as an API.

After action 111, method 100 further includes a crystallization action (not shown in FIG. 1) to produce the solid form of the RHI by using any suitable crystallization techniques, such as applying zinc and vacuum drying. With action 111, the highly purified RHI is in a solid form.

Accordingly, method 100 produces highly purified RHI API, having a purity of 99.0% (w/w) or more, a Total Impurity of 0.8% (w/w) or less, and impurity C of 0.1% (w/w) or less, based on the total weight of the highly purified RHI API, as shown in Examples 1-8 below. Additionally, as shown in Examples 1-4 and 7-8, method 100 can produce RHI API, having a purity of 99.0% (w/w) or more, a Total Impurity of 0.8% (w/w) or less, impurity C of 0.1% (w/w) or less, and impurity E of 0.2% (w/w) or less, all based on the total weight of the highly purified RHI API. This highly purified RHI is suitable for use as an API because of its high purity and low impurity profile. In addition, RHI API is in a solid form.

EXAMPLES

Examples 1-4: Disclosed Methods Produced Highly Purified RHI API Having Purity of 99.0% or More, Total Impurity of 0.8% or Less, and Impurity C of 0.1% or Less Examples 1-4 used method 100 to produce highly purified RHI API, in solid form, having purity of 99.0% (w/w) or more, a Total Impurity of 0.8% (w/w) or less, and impurity C of 0.1% (w/w) or less, based on the total weight of the highly purified RHI API in solid form, as shown in Table 1 below. In Table 1, the Total Impurity includes Impurity C, Impurity X4, Impurity D, Impurity E, and Impurity Z. The Total Impurity does not include the related substance desamido $Asn^{A21}$-RHI. Table 2 identifies the RHI impurity types identified in Table 1, and the percentages of purity and impurities are based on w/w using the total weight of the highly purified solid RHI API. In Table 1, the purity and impurity percentages (w/w) of the solid RHI API were assessed shortly after the purified RHI API was crystallized into solid form.

Also, unexpectedly, in Examples 1-4, method 100 reduced the amount of impurity E to 0.2% (w/w) or less, and as low as 0.12% (w/w), and an average of 0.15% (w/w) of less. Note that Examples 1-4 unexpectedly reduced the amount of impurity E without utilizing the optional water dilution step in action 110 of method 100.

TABLE 1

Impurity Profile of Examples 1-4-Highly Purified RHI API in Solid Form

| Example No. | 1 | 2 | 3 | 4 | Average of Examples 1-4 |
|---|---|---|---|---|---|
| Column Chromatography (internal diameter × length) | 21.2 mm × 250 mm | 21.2 mm × 250 mm | 10.0 mm × 250 mm | 10.0 mm × 250 mm | |
| Purity (w/w) | 99.54% | 99.32% | 99.48% | 99.36% | 99.43% |
| Impurity C (w/w) | n. d | 0.05% | n. d | 0.07% | n.d. (because average is 0.03%, which is below 0.05%) |
| Impurity X4 (w/w) | 0.06% | 0.09% | 0.07% | 0.08% | 0.08% |
| Impurity D (w/w) | n. d | 0.06% | n. d | n. d | n.d. (because average is 0.02%, which is below 0.05%) |

TABLE 1-continued

Impurity Profile of Examples 1-4-Highly Purified RHI API in Solid Form

| Example No. | 1 | 2 | 3 | 4 | Average of Examples 1-4 |
|---|---|---|---|---|---|
| Impurity E (w/w) | 0.12% | 0.15% | 0.13% | 0.18% | 0.15% |
| Impurity Z (w/w) | 0.05% | 0.13% | 0.11% | 0.12% | 0.10% |
| Related Substance-Desamido Asn$^{421}$-RHI (w/w) | 0.23% | 0.20% | 0.21% | 0.21% | 0.21% |
| Total Impurities (w/w) | 0.23% | 0.48% | 0.31% | 0.45% | 0.33% |

In Table 1, n. d. refers to not detected and/or <0.05%.

TABLE 2

Impurities Identified in Table 1

| RHI-Impurity Type | Identity |
|---|---|
| Impurity C | Acetylated Lys$^{B31}$-RHI |
| Impurity X4 | Not identified* |
| Impurity D | Methylated-RHI |
| Impurity E | Thr$^{B30}$ deletion-RHI |
| Impurity Z | High molecular weight product (HMWP)-dimer or multimer |
| Impurity B + X | Impurity B is Lys-RHI and Impurity X is a peak within Impurity B. |

*Impurity X4 is not identified because the impurity is less than 0.10% (w/w). The FDA does not generally require impurity identification when the impurity is less than 0.1% (w/w).

To illustrate the significant technical advancement achieved by the present disclosure, Comparative Examples 1-3 are provided below to show that routine purification techniques could not produce highly purified RHI API having a purity of 99.0% (w/w) or greater, a Total Impurity of 0.8% (w/w) or less, and impurity C of 0.1% (w/w) or less, based on the total weight of the highly purified RHI API.

Comparative Example 1—Alternative Method for Preparing RHI with Less Purity

Comparative Example 1 is an alternative method of producing RHI API and is provided in FIG. 3 as method 300. As shown in FIG. 3, action 301 is the refolding of the preproinsulin using refolding buffers. Comparative Example 1 is based on the RHI produced using at least some of the methods disclosed in Ferring.

At action 302, a Lysine protecting group, citraconic anhydride, ert-Butyloxycarbonyl (Boc), Benzyloxycarbonyl (Cbz, Z), or Allyloxycarbonyl (Alloc). is applied to the proinsulin to protect the Lysine residues present in the proinsulin, which are present at Lys$^{C1}$ of the C-peptide and Lys$^{B29}$ of the B-chain.

Action 303 is a first enzyme cleavage action. At action 303, trypsin is applied to the proinsulin. At action 303, trypsin cleaves: (i) the peptide bond between Arg$^{R1}$ of the leader peptide sequence and Phe$^{B1}$ of the B-chain, and (ii) the peptide bond between Gly$^{A1}$ of A-chain to Arg$^{C2}$ of the C-peptide. Thus, after this first enzyme digestion action, Arg$^{R1}$ is no longer bonded to Phe$^{B1}$, and Gly$^{A1}$ is no longer bonded to Arg$^{C2}$. However, even though Gly$^{A1}$ is no longer bonded to Arg$^{C2}$, the A-chain is still bonded to the B-chain because of the disulfide bonds formed at Cys$^{A7}$-Cys$^{B7}$ and Cys$^{A20}$-Cys$^{B19}$, as described in refolding action 301.

Action 304 is a first column purification action. At action 304, the first column purification action is an anion-exchange column chromatography to separate the cleaved leader peptide sequence from the Arg$^{C2}$-Lys$^{C1}$-RHI. Thus, at the end of action 304, the batch continuing onto the next actions contains primarily Arg-Lys-RHI and impurities.

At action 305, the Lysine residues at Lys$^{C1}$ and Lys$^{B29}$ are de-protected by removing the Lysine protecting group. Thus, the Lysine residues at Lys$^{C1}$ and Lys$^{B29}$ are no longer protected and susceptible to enzyme cleavage.

Optionally, at action 306, aprotinin is applied to eliminate the trypsin leftover from action 303.

Action 307 is a second column purification action, which is an anion-exchange column chromatography to separate the C-peptide from RHI. At the end of action 307, the batch continuing onto the next actions contains primarily RHI and impurities, such as impurity C.

Action 308 is a second enzyme cleavage action. At action 308, because Lys is no longer protected, CPB cleaves the peptide bond between Lys$^{C1}$ and Thr$^{B30}$ thus disconnecting the C-peptide from B-chain, and producing RHI.

Action 309 is a third column purification action. At action 309, a reverse phase high performance liquid chromatography (RP-HPLC), using a C18 column, is applied to remove the C-peptide and other impurities to produce RHI. The RHI was then crystallized into solid form.

Method 300 could only achieve RHI API, in solid form, having a purity of about 97.8% (w/w), a Total Impurity of about 1.7%, impurity C of about 0.5%-0.8% (w/w), and impurity E of about 0.3%-0.5% (w/w), based on the total weight of the RHI API. In Comparative Example 1, the purity and impurity percentages (w/w) of the solid RHI API were assessed shortly after the RHI API was crystallized into the solid form.

Significantly, method 300 differed from method 100 because method 100 includes enzyme digestion action 105 and column purification action 109, which produced an unexpected and surprising result of reduced impurity C, 0.1% (w/w) or less, which in turn enabled the production of highly purified RHI having a purity of 99.0% (w/w) or greater and a Total Impurity of 0.8% (w/w) or less, based on the total weight of the highly purified RHI API. Additionally, method 100 reduced the amount of impurity E to 0.2% (w/w) or less.

TABLE 3

Examples 1-4 (Averaged) versus Comparative Example 1

| Substance | Examples 1-4 (Averaged) | Comparative Example 1 |
|---|---|---|
| Purity of Recombinant Human Insulin (RHI) (w/w) | 99.43% | 97.73% |
| Related Substances (RSub) | 0.21% | 0.53% |
| Desamido Asn$^{421}$-RHI RHI + Rsub (w/w) | 99.64% | 98.26% |
| Total Impurities (w/w) | 0.33% | 1.73% |
| RSub + Total Impurities (w/w) | 0.54% | 2.26% |

In Table 3, the purity profile of RHI API of Examples 1-4 are averaged, and compared to the purity profile of Comparative Example 1. Significantly, as shown in Table 3, Examples 1-4 had a Total Impurity of about 0.33% (w/w), which is significantly lower than the about 1.73% (w/w) Total Impurity of Comparative Example 1. In Table 3, the percentages of purity and impurities are based on w/w and more particularly w/w using the total weight of the corresponding RHI API.

Comparative Example 2—Alternative Method for Preparing RHI API with Less Purity Comparative Example 2 is provided in FIG. 4 as method 400. Notably, Comparative Examples 1-2 differ primarily because of additional column purification action 407. Thus, in method 400, actions 401-406 are equivalent to actions 301-306, and actions 408-410 are equivalent to actions 307-309, and thus for brevity do not need to be described again. Column purification action 407 is a RP-HPLC using a C18 column similar to action 309. The RHI was crystallized into solid form. In Comparative Example 2, the purity and impurity percentages (w/w) of the solid RHI API were assessed shortly after the RHI API was crystallized into the solid form.

Significantly, even with several column purification actions in method 400, method 400 could not produce highly purified RHI API, in solid form, having a purity of 99.0% (w/w) or greater and impurity C of 0.1% (w/w) or less, based on the total weight of the highly purified RHI API. Instead, method 400 produced RHI API, in solid form, having a purity of about 98.1% (w/w), a Total Impurity of about 1.73% (w/w), and impurity C of about 0.5-0.7% (w/w), based on the total weight of the RHI API.

Comparative Example 3—Alternative Method for Preparing RHI API with Less Purity Comparative Example 3 is provided in FIG. 5 as method 500. Notably, Comparative Examples 1 and 3 differ primarily on the switching of the anion-exchange column actions, action 509 and 307, the RP-HPLC actions, actions 507 and 309. Thus, in method 500, actions 501-506 are equivalent to actions 301-306, action 507 is equivalent to action 309, action 508 is equivalent to action 308, and action 509 is equivalent to action 307, and thus for brevity do not need to be described again. Method 500 could not produce highly purified RHI API, in solid form, having a purity of 99.0% (w/w) or greater and impurity C of 0.1% (w/w) or less based on the total weight of the highly purified RHI API. Instead, method 500 produced RHI API, in solid form, having a purity of about 96.5% (w/w) and impurity C of about 0.5-0.7% (w/w) based on the total weight of the RHI API. In Comparative Example 3, the purity and impurity percentages (w/w) of the solid RHI API were assessed shortly after the RHI API was crystallized into the solid form.

Significantly, Comparative Examples 1-3 show that routine optimization of the column purification actions did not solve the technical problem of significantly reducing impurity C in RHI API. Instead, the unique combination of the enzyme digestion action 105 and column purification action 109, as disclosed in method 100, were instrumental in producing highly purified RHI API, in solid form, having a purity of 99.0% (w/w) or greater, a Total Impurity of 0.8% (w/w) or less, and impurity C of 0.1% (w/w) or less, based on the total weight of the highly purified RHI API in solid form.

Comparative Example 4—"Humulin® R" RHI

"Humulin®R" RHI is a commercially available RHI and is used as Comparative Example 4. In Comparative Example 4, four lots of "Humulin® R" RHI were tested for their purity profile, as shown in Table 4, and compared to Examples 1-4.

TABLE 4

Examples 1-4 (Averaged) versus "Humulin ® R" RHI

| Substance | Examples 1-4 (Averaged) | "Humulin ® R" 4 Lots Average |
|---|---|---|
| Purity of Recombinant Human Insulin (RHI) (w/w) | 99.43% | 98.11% |
| Related Substances (RSub) | 0.21% | 0.24% |
| Desamido Asn$^{421}$-RHI | 99.64% | 98.35% |
| RHI + Rsub (w/w) | | |
| Total Impurities (w/w) | 0.33% | 1.65% |
| RSub + Total Impurities (w/w) | 0.54% | 1.89% |

Significantly, as shown in Table 4, Examples 1-4 had a Total Impurity of about 0.33%, which is significantly lower than the about 1.65% (w/w) Total Impurity of the four lots of "Humulin® R" RHI averaged. In Table 4, the percentage of purity and impurities are based on w/w using the total weight of the corresponding RHI API.

Examples 5-8: Scale-Up Examples of Highly Purified RHI API in Solid Form

To demonstrate the capability of method 100 in a scale up environment, such as large scale manufacturing, method 100 was applied to a column of 100 mm×350 mm, which are represented as Examples 5-8 in Table 5. Refer to Table 2 for the description of the impurities in Table 5. In Table 5, the purity and impurity percentages (w/w) of the RHI API were assessed shortly after the purified RHI API was crystallized into solid form.

TABLE 5

Impurity Profile of Scale-Up Examples 5-8-Highly Purified RHI API in Solid Form.

| Example No. | 5 | 6 | 7 | 8 | Average of Examples 5-8 |
|---|---|---|---|---|---|
| Column Chromatography (internal diameter × length) | 100 mm × 350 mm | 100 mm × 350 mm | 100 mm × 350 mm | 100 mm × 350 mm | |
| Purity (w/w) | 99.16% | 99.29% | 99.20% | 99.31% | 99.24% |
| Impurity C (w/w) | n. d | n. d | n. d | n. d | n.d. |
| Impurity X4 (w/w) | n. d | n. d | n. d | n. d | n.d. |
| Impurity D (w/w) | n. d | 0.06% | n. d | n. d | n.d. |
| Impurity E (w/w) | 0.36% | 0.31% | 0.20% | 0.20% | 0.27% |
| Impurity Z (w/w) | 0.08% | 0.06% | 0.14% | 0.08% | 0.09% |
| Impurity B + X (w/w) | 0.16% | 0.15% | 0.17% | 0.21% | 0.17% |
| Related Substance-Desamido Asn$^{421}$-RHI (w/w) | 0.24% | 0.19% | 0.29% | 0.19% | 0.23% |
| Total Impurities (w/w) | 0.23% | 0.48% | 0.31% | 0.45% | 0.33% |

In Table 5, n. d. refers to not detected and/or <0.05%

As demonstrated in scale up Examples 5-8 in Table 5, method 100 produced highly purified RHI API, in solid form, having purity of 99.0% (w/w) or more, a Total Impurity of 0.8% (w/w) or less, and impurity C of 0.1% (w/w) or less, based on the total weight of the highly purified RHI API in solid form. Also, Examples 7-8 reduced the amount of impurity E to 0.20% (w/w). Note that Examples 7-8 unexpectedly reduced the amount of impurity E without utilizing the optional water dilution step in action 110 of method 100. However, as demonstrated in Example 9, the amount of impurity E may be further reduced using the optional water dilution step in action 110 of method 100.

Example 9—Further Reduce Amount of Impurity E

Optionally, at action 110, RP-HPLC can be diluted with water to further reduce Impurity E. To demonstrate, Example 9 shown in Table 6, is a study that applies water dilution to the RP-HPLC at action 110 to three (3) separate samples by 2 times (2×), 3 times (3×), or 4 times (4×), respectively. As demonstrated in Table 6, as the water dilution times increase in action 110, the impurity E percentage decreases. Therefore, if Examples 1-8 utilize this optional water dilution step in action 110 of method 100, the amount of impurity E can be further reduced.

TABLE 6

Further Reduce Impurity E.

| Sample No. | 1 | 2 | 3 |
|---|---|---|---|
| Lys-RHI (mg/mL) | 4 | 4 | 4 |
| Solvent | | $(NH_4)_2SO_4$/IPA | |
| Times of Water Dilution | 4× | 3× | 2× |
| Stop Point Lys-RHI % | 2.60% | 3.20% | 2.10% |
| Impurity E % | 0.25% | 0.35% | 0.48% |

Compositions for Highly Purified RHI API Having Purity of 99.0% or More, a Total Impurity of 0.8% or Less, and Impurity C of 0.1% or Less.

Also disclosed are compositions for active pharmaceutical ingredient (API) comprising highly purified recombinant human insulin (RHI) having a purity of 99.0% (w/w) or more, a Total Impurity of 0.8% (w/w) or less, and an impurity C of 0.1% (w/w) or less, based on the total weight of the highly purified RHI API, and wherein w/w denotes weight by weight of the highly purified RHI API. As disclosed herein, the Total Impurity does not include the related substance desamido $Asn^{A21}$-RHI, and impurity C is acetylated $Lys^{B31}$-RHI. Examples 1-8 provide exemplary embodiments of such compositions.

Additionally, in other embodiments of the compositions, the highly purified RHI API has a purity of 99.0% (w/w) or greater, a Total Impurity of 0.8% or less, impurity C of 0.1% (w/w) or less, and impurity E of 0.2% (w/w) or less, based on the total weight of the highly purified RHI API. Examples 1-4 and 7-8 provide exemplary embodiments of such compositions.

In some embodiments of the compositions, the highly purified RHI API has a purity of 99.3% (w/w) or more based on the total weight of the highly purified RHI API. In some embodiments, the highly purified RHI API composition is in a solid form. In other embodiments, the highly purified RHI API composition is in a liquid form, such as an aqueous form. Exemplary embodiments of these API compositions are provided in Examples 1-8 and these API compositions can be produced using method 100.

The disclosed highly purified API RHI compositions will provide the basis for developing recombinant human insulin drug products with high purity and less impurity, such as recombinant human insulin drug formulations for subcutaneous or intravenous injection.

What is claimed is:

1. A method for producing highly purified recombinant human insulin (RHI) active pharmaceutical ingredient (API), the method comprising:
protecting two Lysine residues on a single-chain precursor (SCP) using a Lysine protecting group, wherein the SCP has a formula of [(Leader Peptide)-(B-Chain)-(C-peptide)-(A-Chain)], wherein the C-peptide is a short peptide consisting of $Arg^{C2}$-$Lys^{C1}$, wherein the two Lysine residues are a first Lysine residue at a first residue of the C-peptide (C1) of the SCP ($Lys^{C1}$), and a second Lysine residue at residue 28 of the B-chain (B28) of the SCP ($Lys^{B28}$);
enzyme-cleaving the SCP to produce an $Arg^{C2}$-$Lys^{C1}$-RHI;
applying a first column purification action to separate the Leader Peptide from the $Arg^{C2}$-$Lys^{C1}$-RHI to generate $Arg^{C2}$-$Lys^{C1}$-RHI;
enzyme-cleaving a half of the C-peptide in the $Arg^{C2}$-$Lys^{C1}$-RHI to produce $Lys^{C1}$-RHI and an Impurity C, wherein the Impurity C is acetylated $Lys^{B31}$-RHI;
de-protecting the two Lysine residues in the $Lys^{C1}$-RHI;
applying a second column purification action to separate one or more impurities from the $Lys^{C1}$-RHI;
applying a third column purification action to the $Lys^{C1}$-RHI to reduce an amount of the Impurity C in the $Lys^{C1}$-RHI to 0.1% (w/w) or less based on the total weight of the $Lys^{C1}$-RHI;
enzyme-cleaving the $Lys^{C1}$-RHI to produce $Lys^{C1}$ and the RHI;
applying a fourth column purification action to separate one or more impurities from the RHI to produce highly purified RHI for use as an API; and
crystallizing the highly purified RHI API to produce highly purified RHI API in a solid form;
wherein the method produces highly purified RHI API, in a solid form, having a purity of 99.0% (w/w) or more, a total impurity of 0.8% (w/w) or less, wherein the total impurity does not include desamido $Asn^{A21}$-RHI, and the Impurity C of 0.1% (w/w) or less, and wherein w/w denotes weight by weight and is based on the total weight of the highly purified RHI API in the solid form.

2. The method of claim 1, wherein the highly purified RHI API, in the solid form, has a purity of 99.3% (w/w) or more, the total impurity of 0.5% (w/w) or less, the total impurity does not include desamido $Asn^{A21}$-RHI, and the Impurity C of 0.1% (w/w) or less.

3. The method of claim 1, wherein the step of enzyme-cleaving the half of the C-peptide in the $Arg^{C2}$-$Lys^{C1}$-RHI comprises applying carboxypeptidase B (CPB) to the $Arg^{C2}$-$Lys^{C1}$-RHI to produce $Lys^{C1}$-RHI.

4. The method of claim 3, wherein the step of enzyme-cleaving the $Arg^{C2}$-$Lys^{C1}$-RHI comprises applying the CPB to the $Arg^{C2}$-$Lys^{C1}$-RHI at a pH of about 8.0 to about 10.0.

5. The method of claim 1, wherein the third column purification action that reduces the amount of the Impurity C to 0.1% (w/w) or less comprises applying reverse-phase high performance liquid chromatography (RP-HPLC) utilizing a C18 column to separate the Impurity C from the $Lys^{C1}$-RHI.

6. The method of claim 5, wherein the third column purification action that reduces the amount of the Impurity C to 0.1% (w/w) or less further comprises utilizing an aqueous solution comprising $(NH_4)_2SO_4$, isopropyl alcohol (IPA), or a combination thereof in the RP-HPLC.

7. The method of claim 5, wherein the third column purification action that reduces the amount of the Impurity C to 0.1% (w/w) or less is carried out at a pH of about 2.5 to about 3.0.

8. The method of claim 5, wherein the RP-HPLC utilizes a preparation column.

9. The method of claim 5, wherein the RP-HPLC utilizes a semi-preparation column.

10. The method of claim 1, wherein the first column purification action and the second column purification action each utilizes anion-exchange column chromatography.

11. The method of claim 1, wherein the third column purification action and the fourth column purification action each utilizes RP-HPLC.

12. The method of claim 11, wherein the third column purification action and the fourth column purification action each utilizes RP-HPLC having a C18 column.

13. The method of claim 11, wherein the third column purification action and the fourth column purification action each utilizes RP-HPLC having a C8 column.

14. The method of claim 1, wherein the Lysine protecting group comprises citraconic anhydride, tert-Butyloxycarbonyl (Boc), Benzyloxycarbonyl (Cbz, Z), Allyloxycarbonyl (Alloc), or a combination thereof.

15. The method of claim 1, wherein the step of enzyme-cleaving the SCP to produce the $Arg^{C2}$-$Lys^{C1}$-RHI comprises applying trypsin to the SCP.

16. The method of claim 15, further comprising removing the trypsin using aprotinin.

17. The method of claim 1, wherein the step of enzyme-cleaving the $Lys^{C1}$-RHI to produce RHI comprises applying CPB.

18. The method of claim 1, further comprising refolding the SCP using a refolding buffer.

19. The method of claim 1, wherein the one or more impurities separated at the second column purification action comprise at least $Arg^{C2}$.

20. The method of claim 1, wherein the one or more impurities separated at the fourth column purification action comprise at least $Lys^{C1}$.

21. The method of claim 1, wherein the method further reduces an amount of impurity E to 0.2% (w/w) or less, wherein the impurity E is $Thr^{B30}$ deletion-RHI, thereby producing highly purified RHI API having a purity of 99.0% (w/w), total impurity of 0.8% (w/w) or less, Impurity C of 0.1% (w/w) or less, and impurity E of 0.2% (w/w) or less, based on the total weight of the highly purified RHI API in the solid form or liquid form, respectively.

22. A method for producing highly purified recombinant human insulin (RHI), the method comprising:
protecting at least two Lysine residues on a single-chain precursor (SCP) using a Lysine protecting group, wherein the SCP has a formula of [(Leader Peptide)-(B-Chain)-(C-peptide)-(A-Chain)], wherein the C-peptide comprises at least $Arg^{C2}$-$Lys^{C1}$, wherein the Lysine residues comprise a first Lysine residue at a first residue of the C-peptide (C1) of the SCP ($Lys^{C1}$), and a second Lysine residue at residue 28 of the B-chain (B28) of the SCP ($Lys^{B28}$);
enzyme-cleaving the $Arg^{C2}$-$Lys^{C1}$-RHI to produce $Lys^{C1}$-RHI and an Impurity C, wherein the Impurity C is acetylated $Lys^{B31}$-RHI;
de-protecting the Lysine residues in $Lys^{C1}$-RHI;
applying a plurality of column purification actions to produce highly purified RHI for use as an API, wherein at least one of the column purification actions reduces an amount of the Impurity C in the $Lys^{C1}$-RHI to 0.1% (w/w) or less based on the total weight of the $Lys^{C1}$-RHI;

enzyme-cleaving the $Lys^{C1}$-RHI to produce RHI; and crystallizing the highly purified RHI API to produce highly purified RHI API in a solid form;

wherein the method produces highly purified RHI API, in a solid form, having a purity of 99.0% (w/w) or more, a total impurity of 0.8% (w/w) or less, wherein the total impurity does not include desamido $Asn^{A21}$-RHI, and the Impurity C of 0.1% (w/w) or less, and wherein w/w denotes weight by weight and is based on the total weight of the highly purified RHI API in the solid form.

23. The method of claim 22, wherein the plurality of column purification actions comprise:
- a first column purification action to separate at least the Leader Peptide from the $Arg^{C2}$-$Lys^{C1}$-RHI, wherein the first column purification action occurs after the step of enzyme-cleaving the SCP to produce the $Arg^{C2}$-$Lys^{C1}$-RHI but before the step of enzyme-cleaving the $Arg^{C2}$-$Lys^{C1}$-RHI to produce the $Lys^{C1}$-RHI and the Impurity C;
- a second column purification action to separate at least $Arg^{C2}$ from the $Lys^{C1}$-RHI, wherein the second purification action separates one or more impurities after the step of de-protecting the Lysine residues in the $Lys^{C1}$-RHI;
- a third column purification action, which is the column purification action that reduces the amount of the Impurity C to 0.1% (w/w) or less in the $Lys^{C1}$-RHI, and this third column purification action occurs after the step of de-protecting the Lysine residues in the $Lys^{C1}$-RHI but before the step of enzyme-cleaving of the $Lys^{C1}$-RHI to produce the RHI; and
- a fourth column purification action to separate at least $Lys^{C1}$ from the RHI, wherein the fourth column purification action occurs after the step of enzyme-cleaving the $Lys^{C1}$-RHI.

24. The method of claim 22, wherein the C-peptide comprises the $Lys^{C1}$, the $Arg^{C2}$, and an Arg as a last residue of the C-peptide that bonds to $Gly^{A1}$ of the A-chain.

25. The method of claim 22, wherein the method further reduces an amount of impurity E to 0.2% (w/w) or less, wherein the impurity E is $Thr^{B30}$ deletion-RHI, thereby producing highly purified RHI API having a purity of 99.0% (w/w), total impurity of 0.8% (w/w) or less, Impurity C of 0.1% (w/w) or less, and impurity E of 0.2% (w/w) or less, based on the total weight of the highly purified RHI API in the solid form or liquid form, respectively.

26. A method for producing highly purified recombinant human insulin (RHI), the method comprising:
- protecting at least two Lysine residues on a single-chain precursor (SCP) using a Lysine protecting group, wherein the SCP has a formula of [(Leader Peptide)-(B-Chain)-(C-peptide)-(A-Chain)], wherein the C-peptide comprises at least $Arg^{C2}$-$Lys^{C1}$, wherein the Lysine residues comprise a first Lysine residue at a first residue of the C-peptide (C1) of the SCP ($Lys^{C1}$), and a second Lysine residue at residue 28 of the B-chain (B28) of the SCP ($Lys^{B28}$);
- enzyme-cleaving the $Arg^{C2}$-$Lys^{C1}$-RHI to produce $Lys^{C1}$-RHI and an Impurity C, wherein the Impurity C is acetylated $Lys^{B31}$-RHI;
- de-protecting the Lysine residues in $Lys^{C1}$-RHI;
- applying a plurality of column purification actions to produce highly purified RHI for use as an API, wherein at least one of the column purification actions reduces an amount of the Impurity C in the $Lys^{C1}$-RHI to 0.1% (w/w) or less based on the total weight of the $Lys^{C1}$-RHI; and enzyme-cleaving the $Lys^{C1}$-RHI to produce RHI;

wherein the method produces highly purified RHI API, in a liquid form, having a purity of 99.0% (w/w) or more, a total impurity of 0.8% (w/w) or less, wherein the total impurity does not include desamido $Asn^{A21}$-RHI, and the Impurity C of 0.1% (w/w) or less, and wherein w/w denotes weight by weight and is based on the total weight of the highly purified RHI API in the liquid form.

27. The method of claim 26, wherein the plurality of column purification actions comprise:
- a first column purification action to separate at least the Leader Peptide from the $Arg^{C2}$-$Lys^{C1}$-RHI, wherein the first column purification action occurs after the step of enzyme-cleaving the SCP to produce the $Arg^{C2}$-$Lys^{C1}$-RHI but before the step of enzyme-cleaving the $Arg^{C2}$-$Lys^{C1}$-RHI to produce the $Lys^{C1}$-RHI and the Impurity C;
- a second column purification action to separate at least $Arg^{C2}$ from the $Lys^{C1}$-RHI, wherein the second purification action separates one or more impurities after the step of de-protecting the Lysine residues in the $Lys^{C1}$-RHI;
- a third column purification action, which is the column purification action that reduces the amount of the Impurity C to 0.1% (w/w) or less in the $Lys^{C1}$-RHI, and this third column purification action occurs after the step of de-protecting the Lysine residues in the $Lys^{C1}$-RHI but before the step of enzyme-cleaving of the $Lys^{C1}$-RHI to produce the RHI; and
- a fourth column purification action to separate at least $Lys^{C1}$ from the RHI, wherein the fourth column purification action occurs after the step of enzyme-cleaving the $Lys^{C1}$-RHI.

28. The method of claim 26, wherein the C-peptide comprises the $Lys^{C1}$, the $Arg^{C2}$, and an Arg as a last residue of the C-peptide that bonds to $Gly^{A1}$ of the A-chain.

29. The method of claim 26, wherein the method further reduces an amount of impurity E to 0.2% (w/w) or less, wherein the impurity E is $Thr^{B30}$ deletion-RHI, thereby producing highly purified RHI API having a purity of 99.0% (w/w), total impurity of 0.8% (w/w) or less, Impurity C of 0.1% (w/w) or less, and impurity E of 0.2% (w/w) or less, based on the total weight of the highly purified RHI API in the solid form or liquid form, respectively.

30. The method of claim 29, wherein at the step of enzyme-cleaving the $Lys^{C1}$-RHI to produce RHI, a water dilution of at least two times is applied at this step to further reduce the amount of impurity E to 0.2% (w/w) or less.

31. A composition comprising:
- a highly purified recombinant human insulin (RHI) active pharmaceutical ingredient (API) comprising:
  - a purity of 99.0% (w/w) or more,
  - a total impurity of 0.8% (w/w) or less, wherein the total impurity does not include desamido $Asn^{A21}$-RHI, and
  - an Impurity C of 0.1% (w/w) or less, wherein the Impurity C is acetylated $Lys^{B31}$-RHI,
- wherein w/w denotes weight by weight and is based on the total weight of the highly purified RHI API.

32. The composition of claim 31, wherein the highly purified RHI API is in a solid form.

33. The composition of claim 31, wherein the highly purified RHI API is in a liquid form.

34. The composition of claim 31, wherein the highly purified RHI API has a purity of 99.3% (w/w) or more, the total impurity is 0.5% (w/w) or less, the total impurity does not include desamido Asn$^{A21}$-RHI, and the Impurity C is 0.1% (w/w) or less, based on the total weight of the highly purified RHI API.

35. The composition of claim 31, wherein the highly purified RHI API has a purity of 99.0% (w/w) or more, the total impurity is 0.8% (w/w) or less, the Impurity C is 0.1% (w/w) or less, and an impurity E is 0.2% (w/w) or less, based on the total weight of the highly purified RHI API, and wherein the impurity E is Thr$^{B30}$ deletion-RHI.

* * * * *

SEQUENCE LISTING

<160> NUMBER OF SEQ ID NOS: 11

<210> SEQ ID NO 1
<211> LENGTH: 21
<212> TYPE: PRT
<213> ORGANISM: Homo sapiens
<220> FEATURE:
<221> NAME/KEY: MISC_FEATURE
<223> OTHER INFORMATION: Native human insulin A chain.

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens
<220> FEATURE:
<221> NAME/KEY: MISC_FEATURE
<223> OTHER INFORMATION: Native human insulin B chain.

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr

```
<210> SEQ ID NO 3
<211> LENGTH: 2
<212> TYPE: PRT
<213> ORGANISM: Artificial Sequence
<220> FEATURE:
<223> OTHER INFORMATION: C-peptide

<400> SEQUENCE: 3

Lys Arg
1

<210> SEQ ID NO 4
<211> LENGTH: 3
<212> TYPE: PRT
<213> ORGANISM: Artificial Sequence
<220> FEATURE:
<223> OTHER INFORMATION: C-peptide

<400> SEQUENCE: 4

Lys Arg Arg
1

<210> SEQ ID NO 5
<211> LENGTH: 5
<212> TYPE: PRT
<213> ORGANISM: Artificial Sequence
<220> FEATURE:
<223> OTHER INFORMATION: C-Peptide

<400> SEQUENCE: 5

Lys Arg Gln Gly Arg
1               5

<210> SEQ ID NO 6
<211> LENGTH: 125
<212> TYPE: PRT
<213> ORGANISM: Artificial Sequence
<220> FEATURE:
<223> OTHER INFORMATION: Synthetic sequence: [(Leader
      Peptide)-(B-Chain)-(C-peptide)-(A-Chain)]
<220> FEATURE:
<221> NAME/KEY: VARIANT
<222> LOCATION: (2)..(2)
<223> OTHER INFORMATION: Xaa can be any naturally occurring amino acid.
<220> FEATURE:
<221> NAME/KEY: VARIANT
<222> LOCATION: (3)..(71)
<223> OTHER INFORMATION: Xaa can be any naturally occurring amino acid
      or may be absent.

<400> SEQUENCE: 6

Ala Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Arg Phe Val Asn Gln His Leu Cys Gly
65                  70                  75                  80

Ser His Leu Val Glu Ala Leu Tyr Leu Val Cys Gly Glu Arg Gly Phe
                85                  90                  95
```

Phe Tyr Thr Pro Lys Thr Lys Arg Gly Ile Val Glu Gln Cys Cys Thr
                100                 105                 110

Ser Ile Cys Ser Leu Tyr Gln Leu Glu Asn Tyr Cys Asn
        115                 120                 125

<210> SEQ ID NO 7
<211> LENGTH: 126
<212> TYPE: PRT
<213> ORGANISM: Artificial Sequence
<220> FEATURE:
<223> OTHER INFORMATION: Synthetic sequence: [(Leader
      Peptide)-(B-Chain)-(C-peptide)-(A-Chain)]
<220> FEATURE:
<221> NAME/KEY: VARIANT
<222> LOCATION: (2)..(2)
<223> OTHER INFORMATION: Xaa can be any naturally occurring amino acid.
<220> FEATURE:
<221> NAME/KEY: VARIANT
<222> LOCATION: (3)..(71)
<223> OTHER INFORMATION: Xaa can be any naturally occurring amino acid
      or may be absent.

<400> SEQUENCE: 7

Ala Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Arg Phe Val Asn Gln His Leu Cys Gly
65                  70                  75                  80

Ser His Leu Val Glu Ala Leu Tyr Leu Val Cys Gly Glu Arg Gly Phe
                85                  90                  95

Phe Tyr Thr Pro Lys Thr Lys Arg Arg Gly Ile Val Glu Gln Cys Cys
                100                 105                 110

Thr Ser Ile Cys Ser Leu Tyr Gln Leu Glu Asn Tyr Cys Asn
            115                 120                 125

<210> SEQ ID NO 8
<211> LENGTH: 129
<212> TYPE: PRT
<213> ORGANISM: Artificial Sequence
<220> FEATURE:
<223> OTHER INFORMATION: Synthetic sequence: [(Leader
      Peptide)-(B-Chain)-(C-peptide)-(A-Chain)]
<220> FEATURE:
<221> NAME/KEY: VARIANT
<222> LOCATION: (2)..(2)
<223> OTHER INFORMATION: Xaa can be any naturally occurring amino acid.
<220> FEATURE:
<221> NAME/KEY: VARIANT
<222> LOCATION: (3)..(71)
<223> OTHER INFORMATION: Xaa can be any naturally occurring amino acid
      or may be absent.

<400> SEQUENCE: 8

Ala Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa
            35                  40                  45

```
Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Arg Phe Val Asn Gln His Leu Cys Gly
65                  70                  75                  80

Ser His Leu Val Glu Ala Leu Tyr Leu Val Cys Gly Glu Arg Gly Phe
                85                  90                  95

Phe Tyr Thr Pro Lys Thr Lys Arg Arg Gln Gly Arg Gly Ile Val Glu
                100                 105                 110

Gln Cys Cys Thr Ser Ile Cys Ser Leu Tyr Gln Leu Glu Asn Tyr Cys
            115                 120                 125

Asn

<210> SEQ ID NO 9
<211> LENGTH: 53
<212> TYPE: PRT
<213> ORGANISM: Artificial Sequence
<220> FEATURE:
<223> OTHER INFORMATION: Synthetic sequence:
      [(B-Chain)-(C-peptide)-(A-Chain)]

<400> SEQUENCE: 9

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Lys Arg
                20                  25                  30

Gly Ile Val Glu Gln Cys Cys Thr Ser Ile Cys Ser Leu Tyr Gln Leu
            35                  40                  45

Glu Asn Tyr Cys Asn
        50

<210> SEQ ID NO 10
<211> LENGTH: 32
<212> TYPE: PRT
<213> ORGANISM: Artificial Sequence
<220> FEATURE:
<223> OTHER INFORMATION: Synthetic sequence: [(B-Chain)-(C-peptide)]

<400> SEQUENCE: 10

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Lys Arg
                20                  25                  30

<210> SEQ ID NO 11
<211> LENGTH: 31
<212> TYPE: PRT
<213> ORGANISM: Artificial Sequence
<220> FEATURE:
<223> OTHER INFORMATION: Synthetic sequence: B-Chain attached to cleaved
      C-peptide fragment

<400> SEQUENCE: 11

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Lys
                20                  25                  30
```